(12) United States Patent
Armbruster et al.

(10) Patent No.: US 6,787,660 B1
(45) Date of Patent: Sep. 7, 2004

(54) FUNCTIONAL VITAMIN D DERIVATIVES AND A METHOD FOR DETERMINING 25-HYDROXY-VITAMIN D AND 1α, DIHYDROXY-VITAMIN D

(75) Inventors: Franz Paul Armbruster, Bobenheim-Roxheim (DE); Wolfgang Voelter, Tübingen (DE); Jens Tampe, München (DE); Christian Birkmayer, München (DE)

(73) Assignees: Immundiagnostik AG, Bensheim (DE); Biomedica GmbH, Vienna (AT)

(*) Notice: Subject to any disclaimer, the term of this patent is extended or adjusted under 35 U.S.C. 154(b) by 0 days.

(21) Appl. No.: 09/720,338

(22) PCT Filed: Jun. 25, 1999

(86) PCT No.: PCT/EP99/04418

§ 371 (c)(1),
(2), (4) Date: Feb. 20, 2001

(87) PCT Pub. No.: WO99/67211

PCT Pub. Date: Dec. 29, 1999

(30) Foreign Application Priority Data

Jun. 25, 1998 (DE) .......................................... 198 28 379
Sep. 4, 1998 (DE) .......................................... 198 40 435

(51) Int. Cl.[7] ..................... C07J 401/00; C07D 235/00
(52) U.S. Cl. ..................................... 552/653; 548/303.7
(58) Field of Search ........................ 552/653; 548/303.7

(56) References Cited

FOREIGN PATENT DOCUMENTS

| EP | 0312360 | 4/1989 |
| WO | 9724127 | 7/1997 |
| WO | WO 97/24127 | * 7/1997 |

OTHER PUBLICATIONS

Roy et al., Steroids, vol. 60(8), pp. 530–533, 1995.*
Swamy et al., Protein Expression and Purifcation, vol. 6(2), pp. 185–188, 1995.*

Kobayashi, N. Et Al.: "Specificity of Polyclonal Antibodies Raised against a Novel 24, 25–Dihydroxyvitamin D3–Bovine Serum Albumin Conjugant Linked through the C–11–alpha or C–3 Position" J. Steroid Biochem. Molec. Biol., vol. 62, No. 1, 1997, pp. 79–87, XP002119849.

Higashi, T. et al. "Enzyme–linked immunosorbent assay for plasma 24,25–dihydroxyvitamin–D3" Analytica Chimica Acta, vol. 365, No. 1–3, 1998, pp. 151–158, XP002119850.

* cited by examiner

Primary Examiner—Barbara P. Badio
(74) Attorney, Agent, or Firm—Birch, Stewart, Kolasch & Birch, LLP

(57) ABSTRACT

Vitamin D compounds of formula (I) with a label attached to a spacer group in the 3 position are disclosed.

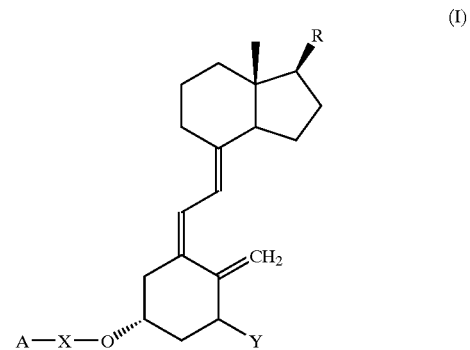

(I)

In the above formula (I), X is an optionally substituted hydrocarbon group with a length of 0.8–4.2 nm, optionally containing the heteroatoms S, O, N or P; Y is H or OH; A is a label capable of binding with high affinity to a protein; R is an optionally substituted hydrocarbon side chain of a D vitamin or a D vitamin metabolite. Also disclosed is the preparation of formula (I).

9 Claims, 15 Drawing Sheets

FUNCTIONAL VITAMIN D DERIVATIVES AND A METHOD FOR DETERMINING 25-HYDROXY-VITAMIN D AND 1α, DIHYDROXY-VITAMIN D

This application is the national phase under 35 U.S.C. § 371 of PCT International Application No. PCT/EP99/04418 which has an International filing date of Jun. 25, 1999, which designated the United States of America.

The invention relates to derivatives of 25-hydroxy vitamin D, a synthesis thereof, and a method of measuring 25-hydroxy vitamin D and 1,25-dihydroxy vitamin D in samples.

The D-vitamins or calciferols arise from their provitamins through a cleavage, catalysed by sunlight, of the B-ring in the sterane rings. Their most important representatives are vitamin $D_3$ (cholecalciferol) and vitamin $D_2$ (ergocalciferol), which differ slightly only in the side chains, but which—so far as known—are similarly metabolised and have identical biological effects. Whereas provitamin $D_2$ must be taken in with the food, the provitamin $D_3$ can be formed in the human organism. So far as not more specifically designated by means of indices, the term vitamin D comprehends in the following in general all vitamin D forms. Vitamin D formed in the skin or taken in with food is bound in the plasma by vitamin D binding or transport proteins (DBP), transported to the liver and there metabolised to 25-hydroxy vitamin D (25-OH-D). The vitamin D binding protein DBP is also known as Gc-globulin or group specific component (J. G. Haddad in J. Steriod Biochem. Molec. Biol. (1995) 53, 579–582). Over 95% of the 25-hydroxy vitamin D measurable in the serum is as a rule 25-hydroxy vitamin $D_3$. 25-Hydroxy vitamin $D_2$ is only found in greater proportions if the person is receiving medication with vitamin $D_2$ or, as is frequently the practice in the United States, foodstuffs are supplemented with vitamin $D_2$.

25-Hydroxy vitamin D is the prevailing vitamin D metabolite in the blood circulation and its concentration in the serum generally indicates the vitamin D status, i.e. the extent to which vitamin D is available to the organism. If needed, 25-hydroxy vitamin D is metabolised in the kidneys to 1α,25-dihydroxy vitamin D, a hormone-like substance with great biological activity. The determination of 1α,25-dihydroxy vitamin D indicates how much vitamin D is present in the activated form.

BACKGROUND OF THE INVENTION

The determination of 25-hydroxy vitamin D in a sample is preferably effected in accordance with the principle of competitive protein binding analysis, whereby on the basis of the displacement of radioactive 25-hydroxy vitamin D from the binding sites of a vitamin D binding protein, the 25-hydroxy vitamin D present in the sample can be quantified. Also, over the last several years, radioimmunoassays using $^{125}$I-labelled vitamin D derivatives and antibodies for vitamin D derivatives have established themselves in diagnosis. The data of the normal level of 25-hydroxy vitamin D in serum vary depending on the laboratory. It is, however, agreed that the concentration of 25-hydroxy vitamin D in the serum is as a rule greater than 5 ng/ml and smaller than 80 ng/ml. The competitive protein binding analysis requires the use of a radioactive vitamin D derivative which must have the same protein binding characteristics as 25-hydroxy vitamin D. The same applies also for the competitive binding analysis for the biologically active 1α,25-dihydroxy vitamin D and other vitamin D metabolites.

European patent specifications 0 312 360 and 0 363 211, and Tanabe et al. in J. Chem. Soc., Chem. Commun. 1989, 1220–1221 and J. Nutri. Sci. Vitaminol., 1991, 37, 139–147, disclose various $^{125}$I-labelled hydroxy- and dihydroxy vitamin D derivatives and their use in binding studies. These derivatives suffer the disadvantages that they are problematic to produce and are extremely labile. Light, radioactive rays, protons, hydrogen, enzymes, free radicals or the presence of iodine in free or bound form have great effect on the configuration and the binding characteristics of the vitamin D derivatives to vitamin D binding protein DBP or specific antibodies. Above all, they can cause or catalyse a rotation of the A-ring in the sterane system. The 3β-hydroxy-group of the vitamin D molecule is thereby rotated into the pseudo-1α-position, so that 5,6-trans-vitamin D is obtained. The so-called pseudo-1α-hydroxy-analogs of vitamin D may be metabolised similarly to vitamin D, but they have a structure which is different in significant points and are not bound or are significantly more poorly bound by vitamin D binding proteins such as for example DBP/Gc-Globulin or anti-vitamin D antibodies.

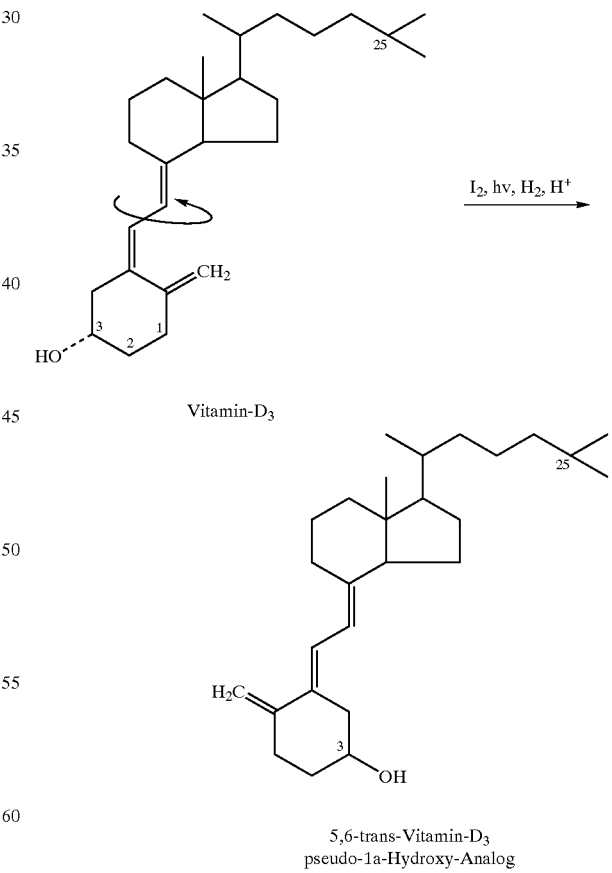

DESCRIPTION OF RELATED ART

The above-described re-arrangement is to be understood as an example. Other chemical reactions and re-arrangements also occur. The same applies for $^3$H- or $^{14}$C-labelled vitamin b derivatives. These vitamin D derivatives are likewise not so stable that they permit a reliable binding analysis. The radioactive marking additionally increases the costs of storage, transport and disposal and is generally disadvantageous for health and the environment. Further the half-life of $^{125}$iodine is relatively short. On the other hand, a competitive binding analysis with $^3$H- and $^{14}$C-labelled vitamin D derivatives requires particular scintillation counters and is more demanding in terms of equipment, with largely the same problems.

Ray et al., in Biochemistry, 1991, 30, 4809–4813 disclose the coupling of vitamin $D_3$ with various colouring groups. The detection sensitivity for dye-labelled vitamin $D_3$ derivatives is, however, too small that one might use them in a competitive binding analysis for natural vitamin D metabolites, apart from the fact that the dye-labelled derivatives are not stable in serum and further are particularly light-sensitive.

BRIEF SUMMARY OF THE INVENTION

It is the object of the invention to make available vitamin D derivatives which can be employed in a competitive binding analysis or quite generally in immunoassays of vitamin D metabolites such as 25-hydroxy vitamin D and 1,25-dihydroxy vitamin D. This presumes the following properties: first, that for the vitamin D derivatives, a detection sensitivity exists which is higher than, or lies in a lower range of concentrations than, the concentration of the sought after vitamin D metabolites in the samples; second, that the derivatives are stable in serum, plasma or urine under the usual protonic conditions and are stable with the respect to serum enzymes; and finally, third, that the derivatives are sufficiently stable with regard to light and storage, over weeks and months. This object is achieved by means of vitamin D derivatives having the formula (I)

wherein:
 O represents the oxygen atom of an ether group;
 X represents a substituted or non-substituted hydrocarbon group of 0.8 to 4.2 nm length, preferably a C8- to C12-group, which may have the usual heteroatoms such as S, O, N or P, most particularly preferred an hexamido-, octamido- or decamido-amidopropylether linker group;
 Y represents hydrogen or a hydroxy group;
 A a functional group which is bound with high affinity by a binding protein such as an antibody or vitamin D binding protein DBP;
 R the side group of a vitamin D metabolite, preferably the side group of vitamin $D_2$ or $D_3$, particularly preferably the 25-hydroxylated side group of vitamin $D_2$ or $D_3$.

A high affinity is present when the dissociation constant (K) between the binding protein, e.g. the antibody or DBP, and the antigen or the functional group A is greater than $10^8$. A dissociation constant greater than $10^{16}$ is advantageous for many applications. In a preferred embodiment A is selected from biotin, digoxigenin, tyrosine, substituted tyrosine, substituted amino acids, characteristic amino acid and peptide sequences, FITC, FITC-substituted tyrbsine, proteins and protein groups such as protein A and protein G or a further vitamin D derivative, most particularly preferred 25-hydroxy vitamin D.

The spacer group X is preferably selected from substituted and non-substituted C-bodies having a length of 0.8 to 4.2 nm, preferably about 0.12 nm. Particularly preferred is an amino carboxylic acid, in particular an amino undecanoic acid, peptide and keto group or a substituted or non-substituted amino polyether radical having a length of 0.8 to 4.2 nm, preferably about 0.9 to 1.5 nm. This spacing between the group A and the binding or detection site for the vitamin D radical is necessary so that the binding proteins can bind to the binding site concerned in each case and thereby do not interfere with one another. It is to be taken into consideration that for example for the vitamin D binding protein DBP (Gc-globulin) the 19-methylene group, if applicable the 1-hydroxy group of the A-ring and the vitamin D side chain belong to the recognition site and are received in a binding pocket. Similar applies also for specific antibodies against the various vitamin D derivatives. If the spacer group X is too short no further binding protein can bind to the selected functional group A along with the vitamin D binding protein. For the preferred example, this means that when the functional biotin group is located within the binding pocket of the vitamin D binding protein it is no longer accessible for the second binding protein, for example the streptavidin. On the other hand, if the spacer group X is too long, molecular folding can arise which likewise hinders the simultaneous binding of two binding partners.

Further, the spacer group in accordance with the invention surprisingly has a steric effect, since it clearly actively hinders a 180° degree rotation of the A-ring. It is suspected, without being restricted to this theory, that the 3β-oxygen atom of the ether group on the A-ring is hydrated corresponding to a natural hydroxy group and so prevents an attack on the 5,6-double bond, apart from other electronic and steric effects. A further important aspect is that the ether group in accordance with the invention cannot be dissociated by the esterases which are always present in serum or plasma.

Most particularly preferred is 25-hydroxy vitamin-$D_3$-3β-3'[6-N-(biotinyl)hexamido]amidopropylether of the formula II

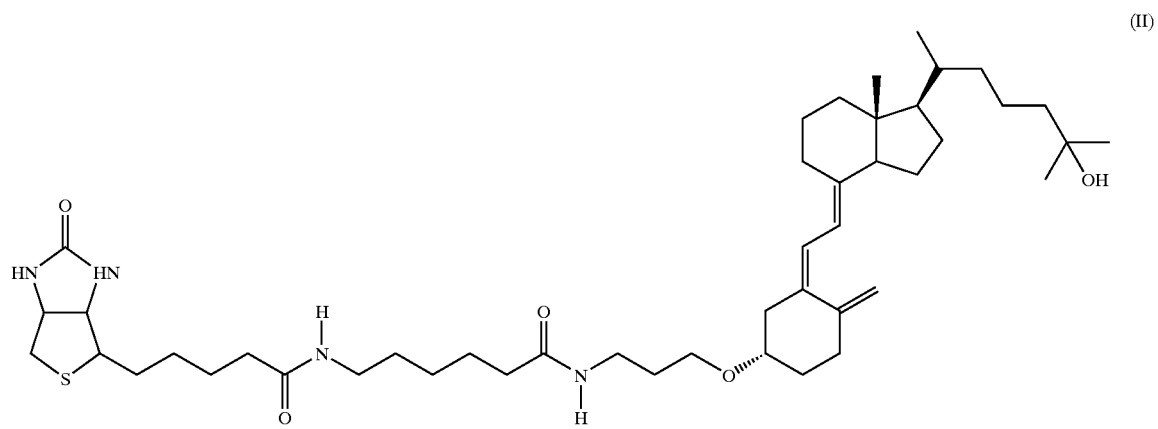

(II)

and the 1α-hydroxy- and vitamin D₂ analogs.

Further preferred are derivatives which contain as the second functional group a vitamin D radical. The advantage of these derivatives is that they contain no groups and compounds foreign to the system and so allow an increased sensitivity and reliability of the competitive binding analysis, also because they compensate, in a quantitative detection, for possible binding peculiarities of first and second binding of the vitamin D binding protein. Particularly preferred are compounds of the following formula III:

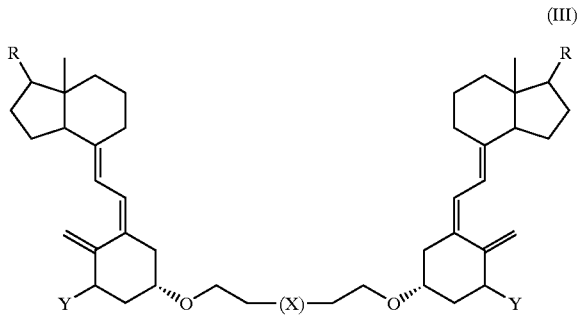

(III)

wherein R, Y and X are defined as in formula I above. Thereby, symmetrical vitamin D derivatives are particularly favourable.

The 25-hydroxy- and 1α,25-dihydroxy vitamin D derivatives in accordance with the invention are surprisingly stable with respect to light, storage and serum and allow in all competitive immune diagnostic methods a sensitive, reliable quantitative determination of vitamin D metabolites such as 25-hydroxy- and 1α,25-dihydroxy vitamin D, for example for routine diagnostic use in human or veterinary medicine and in research.

In accordance with the invention the compound having formula I is obtained by means of a method including the steps: a) cyanoethylation of the 3-hydroxy group of vitamin D or 25-hydroxy vitamin D with acrylonitrile in a suitable solvent such as acetonitrile in the presence of potassium hydride and tertiary butanol; b) reduction of the resulting nitrile group with a mixture of lithium hydrid and lithium aluminium hydride to an amine; and c) linking a spacer group, if appropriate with a functional group A, to the amine, for example biotinylation of the compound with an active biotinylation reagent such as LC-BHNS or, to obtain a vitamin D derivative in accordance with formula III, coupling of two amino-vitamin D groups, by means of condensation, with a dicarboxylic acid such as sebacinic acid, by means of carbodiimide.

The method in accordance with the invention for the production of functional vitamin D derivatives gives higher yields with shorter reaction times. Different from conventional methods, there is effected namely in step a) the cyanoethylation of the 3-hydroxy group in the presence of potassium hydride and tertiary butanol. By this means it is achieved that cyanoethylation is effected only at the 3-hydroxy group of vitamin D and the other hydroxy groups of the vitamin D are protected from reaction. The reaction is effected at 0 to 20° C., preferably at 5 to 8° C. in a neutral solvent medium such as acetonitrile.

In the subsequent reduction, the nitrile group of the cyanoethylether is quantitatively reduced into the amine, which can then be relatively simply linked with another functional group, for example by means of reaction with a commercial available biotinylation reagent.

The invention includes additionally the use of the functional vitamin D derivatives in accordance with the invention in methods for detecting 25-hydroxy- and 1α,25-dihydroxy vitamin D in serum, plasma, urine or another sample. Here, the functional vitamin D conjugate in accordance with the invention is employed either as an intermediate, whereby the vitamin D binding protein and native vitamin D metabolites compete for the binding site, or is employed itself as competitive binding component to native vitamin D. The quantitative detection method is preferably an EIA, ELISA, RIA, IRMA, LiA or ILMA, FIA or IFMA in test systems which are to be worked manually or in versions adapted to automatic testing machines, in liquid phase as well as solid phase technology.

A particularly preferred method for detecting 25-hydroxy- and 1α,25-dihydroxy vitamin D derivatives include the steps: a) coating a carrier with streptavidin, b) addition of one or a plurality of a multifunctional biotin-vitamin D derivatives, c) addition of the sample and a defined quantity of vitamin D binding protein, d) detection of the bound binding protein with labelled anti-vitamin D binding protein antibodies. The labelling of the anti-vitamin D binding protein antibodies can be direct, for example a radioactive marking, or also indirect, for example by an enzyme or an active enzyme fragment such as peroxidase, which is capable of catalysing a colour reaction.

A further preferred method for detecting 25-hydroxy- and 1α,25-dihydroxy vitamin D derivatives includes the steps: a) coating a carrier with anti-vitamin D binding protein antibodies, b) adding the vitamin D binding protein, c)

adding the sample and a defined quantity of biotin-vitamin D derivative, d) detecting the quantity of bound derivative with labelled streptavidin. The streptavidin is preferably indirectly labelled with peroxidase; the carrier is preferably a reaction vial wall, for example of a microtitration plate, or particles of polymer or magnetic material or both, for example plastic or cellulose microparticles.

These methods make possible a non-radioactive quantitative detection of 25-hydroxy- and 1,25-dihydroxy vitamin D, without extensive safety measures being required. The competitive methods proposed here are thus suitable for routine investigations within in the scope of osteoporosis prophylaxis, in the case of a suspected D-hypovitaminosis or D-hypervitaminosis, for diagnostics in general, and in research.

A further aspect of the invention is a kit for detecting vitamin D metabolites such as 25-hydroxy- and 1,25-dihydroxy vitamin D, which inter alia contains the functional vitamin D derivative in accordance with the invention. The kit includes a vitamin D binding protein (Gc-globulin) which can be freely selected, anti-vitamin D binding protein antibodies, streptavidin and pre-prepared or non-pre-prepared microtitration plates and/or magnetic or other microparticles and other reagents.

BRIEF DESCRIPTION OF THE DRAWINGS

Further advantages, features and embodiments of the invention are indicated in the following examples and the accompanying drawings, which show:

FIG. 1 shows the route of synthesis in accordance with the invention for the production of a bifunctional 25-OH vitamin D conjugate. First, 25-OH vitamin D is cyanoethylated in a mixture of acetonitrile, potassium hydride, and tertiary butanol with acrylonitrile. Due to the presence of the potassium hydride, acting as a base, and due to the presence of tertiary butanol for avoiding non-specific reactions at the 25-hydroxy group, it is achieved that the 3-hydroxy group of the vitamin D is selectively cyanoethylated. The yield of 25-OH vitamin D-3β-cyanoethylether amounts, as a rule, to about 74% with a reaction time of 40 minutes.

After conventional preparation, the 25-OH vitamin D-3□ cyanoethylether is mixed with lithium hydride and the 25-hydoxy group converted into the lithium alcoholate. There follows a reduction of the nitrite with $LiAlH_4$, to 25-OH-vitamin-D-3□-3'-amino propylether. This step is quantitative, without by-products arising. Finally there is effected, if necessary, a biotinylation with an active biotinylation reagent such as LC-BHNS (biotinyl -N-ϵ-amino caproyl-hydroxy-succinimide ester). The resulting spacer group X has, corresponding to the amino caproyl chain, a length of about 0.8 to 0.9 nm.

25-OH-vitamin-D-3β-3['6-N-(biotinyl)hexamido] amidopropyl-ether is temperature stable and can be stored over many months in an aqueous, slightly acid matrix. Since the compound can not be cleaved by serum enzymes, it is ideally suited for routine diagnostic tests in serum, plasma and urine.

Figure 2:
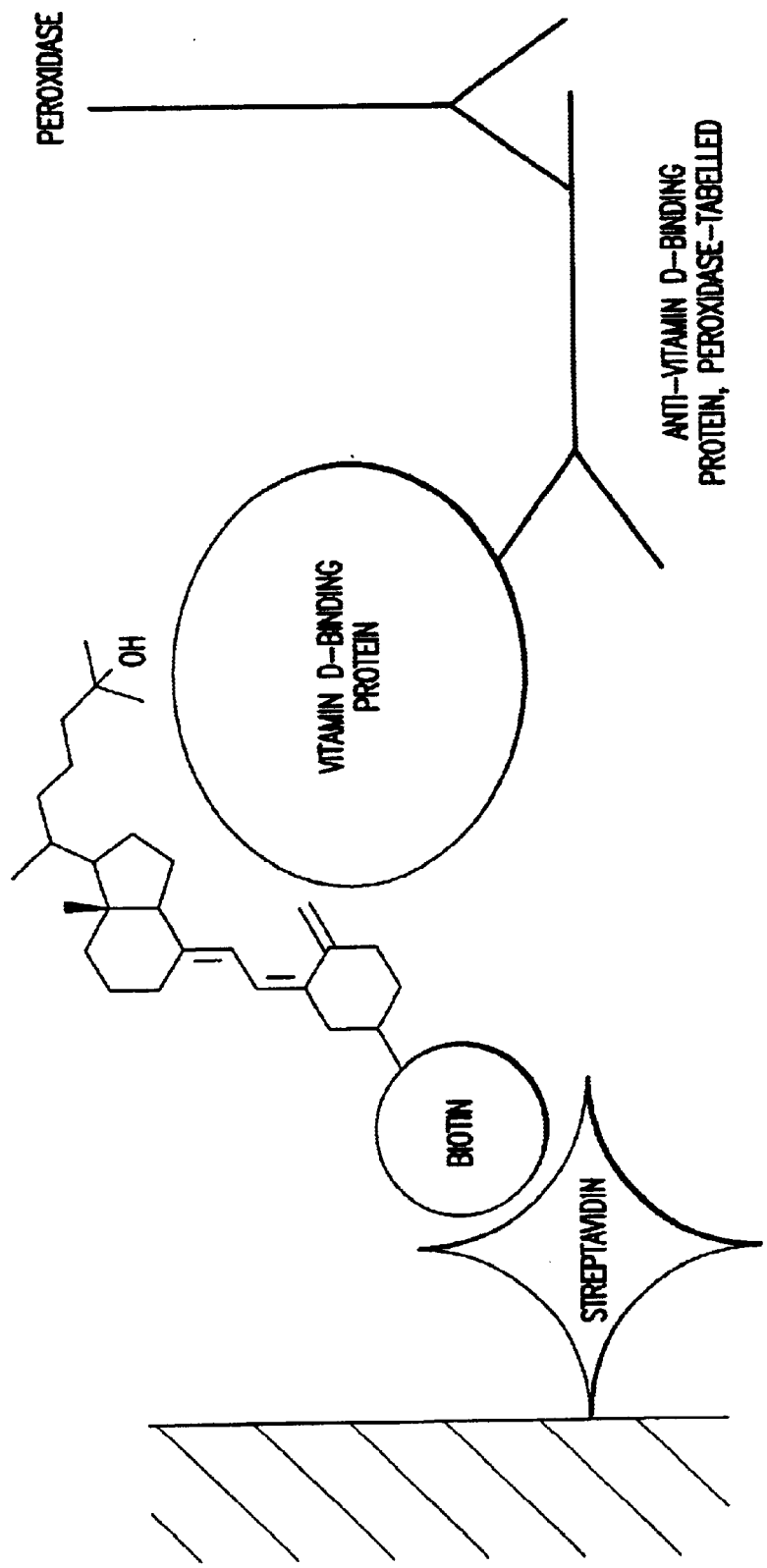
FIGS. 2, 3 and 4 schematic representations of various ELISAs for the detection of 25-OH-vitamin D with the aid of the 25-OH-vitamin D conjugate in accordance with the invention.

FIG. 2 shows a schematic representation of a competitive ELISA for 25-OH-vitamin D. Here, the 25-OH-vitamin D conjugate (25-OH-vitamin-D-3β-3'[6-N-(biotinyl) hexamido]-amidopropylether) is bound via streptavidin to a solid phase. Then, in liquid phase, there is effected the competitive binding of vitamin D binding protein and 25-OH-vitamin D from a standard or a sample to the 25-OH-dihydroxyvitamin D conjugate. The detection is effected by means of peroxidase labelled antibodies against the vitamin D binding protein. The skilled person knows that also other marker enzymes can be employed, for example alkaline phosphatase or galactosidase, etc.

Figure 3:
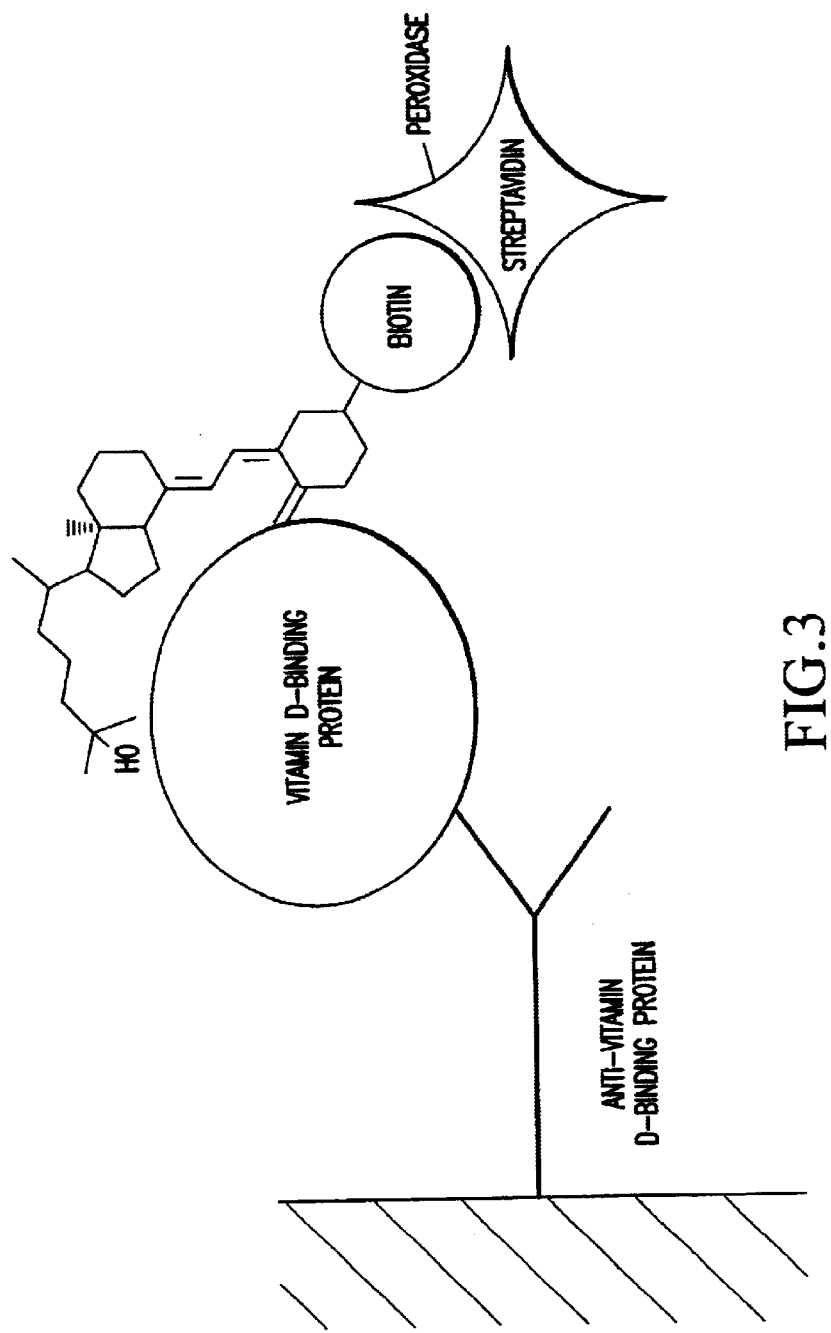

FIG. 3 shows a schematic representation of a competitive, non-radioactive ELISA whereby the vitamin D binding protein is first bound to the solid phase via anti-vitamin D binding protein antibodies. There is then effected, in liquid phase, a competitive binding of 25-OH-vitamin D biotin and 25-OH-vitamin D from a standard or a sample. For detection, peroxidase-labelled streptavidin is then employed. The indicated principle can of course be transferred to other tracer groups instead of biotin and to other marker enzymes, as indicated above.

Figure 4:
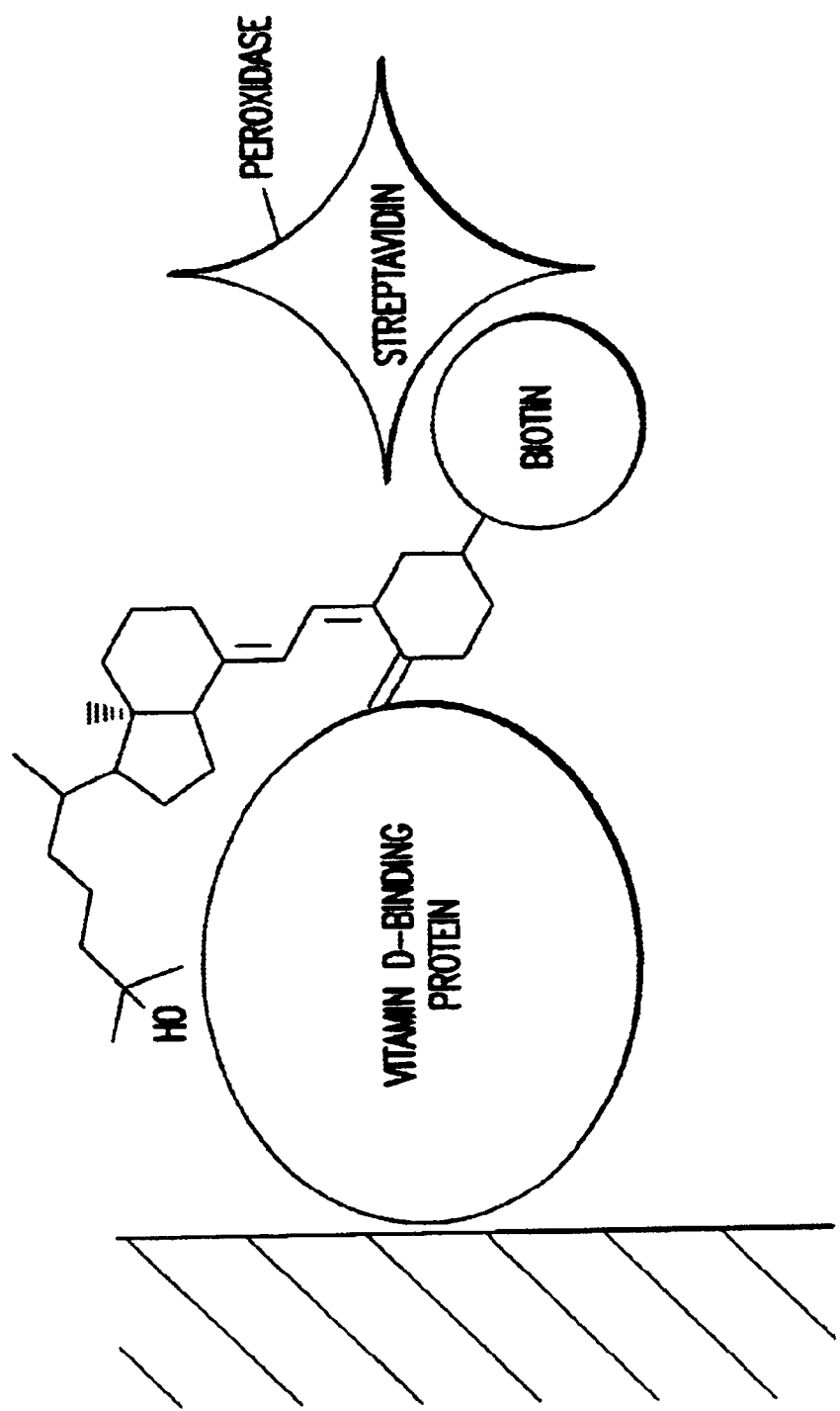

FIG. 4 shows a schematic representation of a competitive ELISA, whereby the vitamin D binding protein is directly bound to the solid phase. The competitive binding of 25-OH-vitamin $D_3$-biotin and 25-OH-vitamin $D_3$ from a standard or a sample is effected in liquid phase and peroxidase-labelled streptavidin is employed for quantitative detection.

Figure 5A:
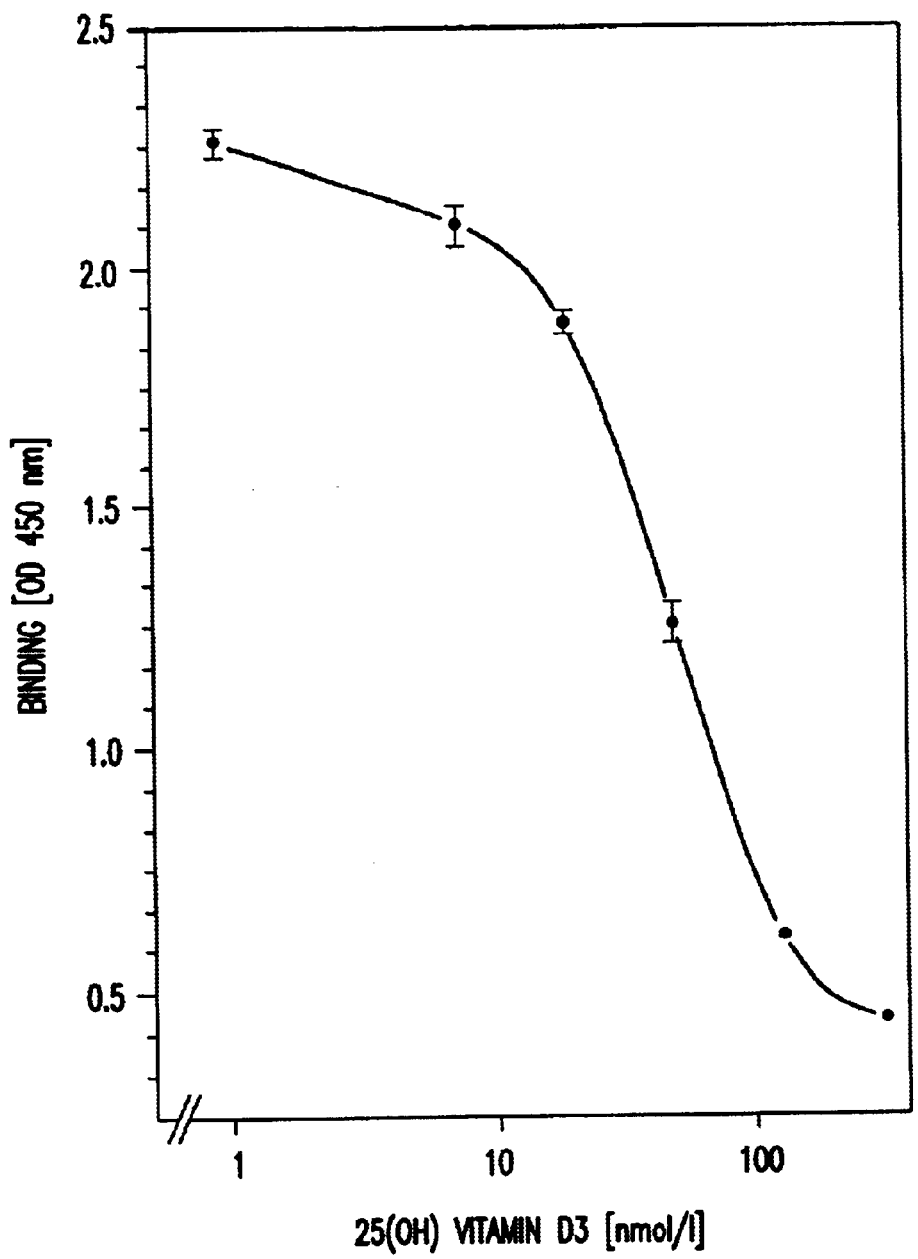
FIG. 5A the calibration curve of a competitive ELISA for 25-OH-vitamin D according to FIG. 2.
Figure 5B:
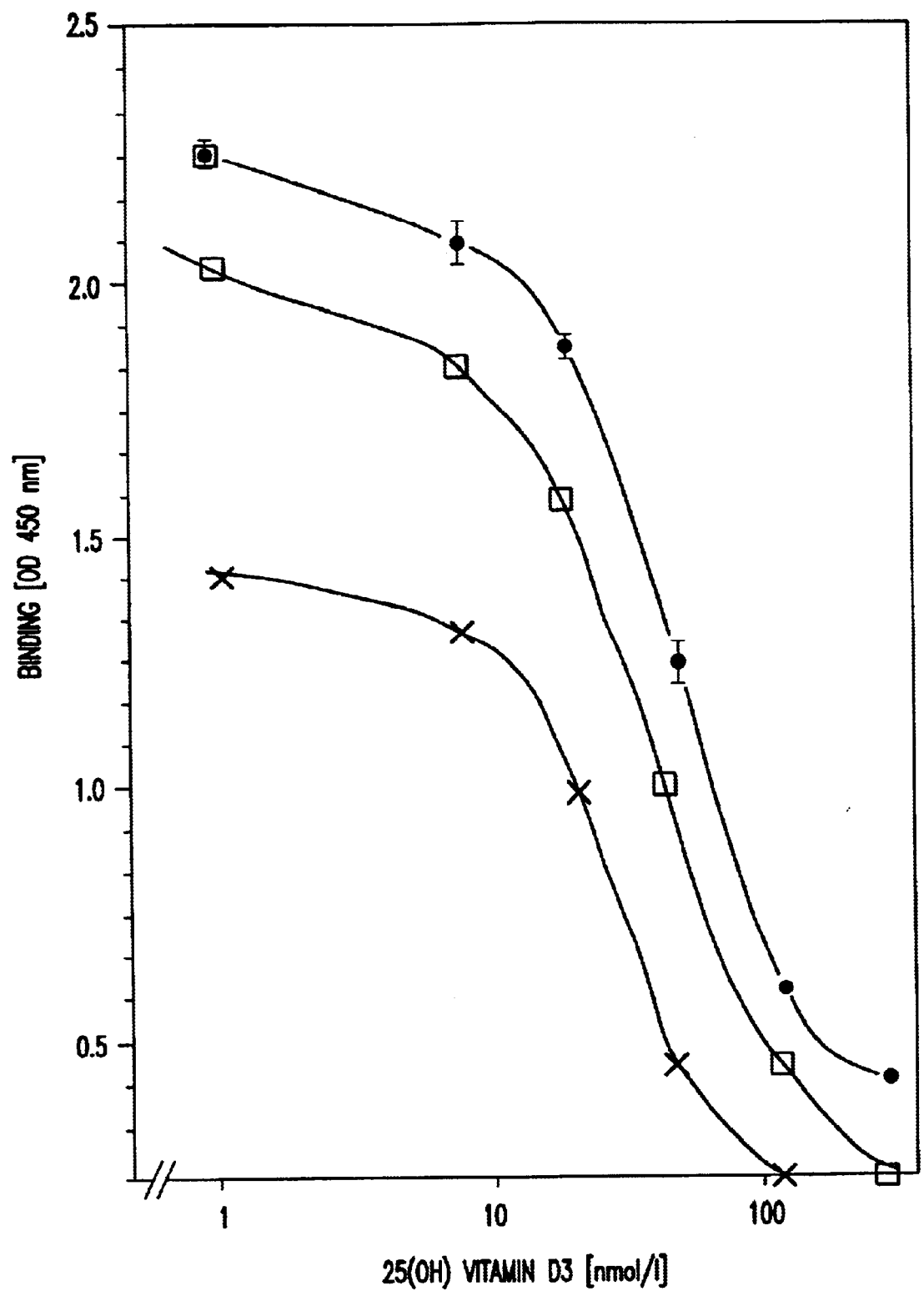
FIG. 5B calibration curves for ELISAs in accordance with FIG. 5A, having 3, 60 and 100 days old 25-OH-vitamin D biotin tracer.
Figure 5C:
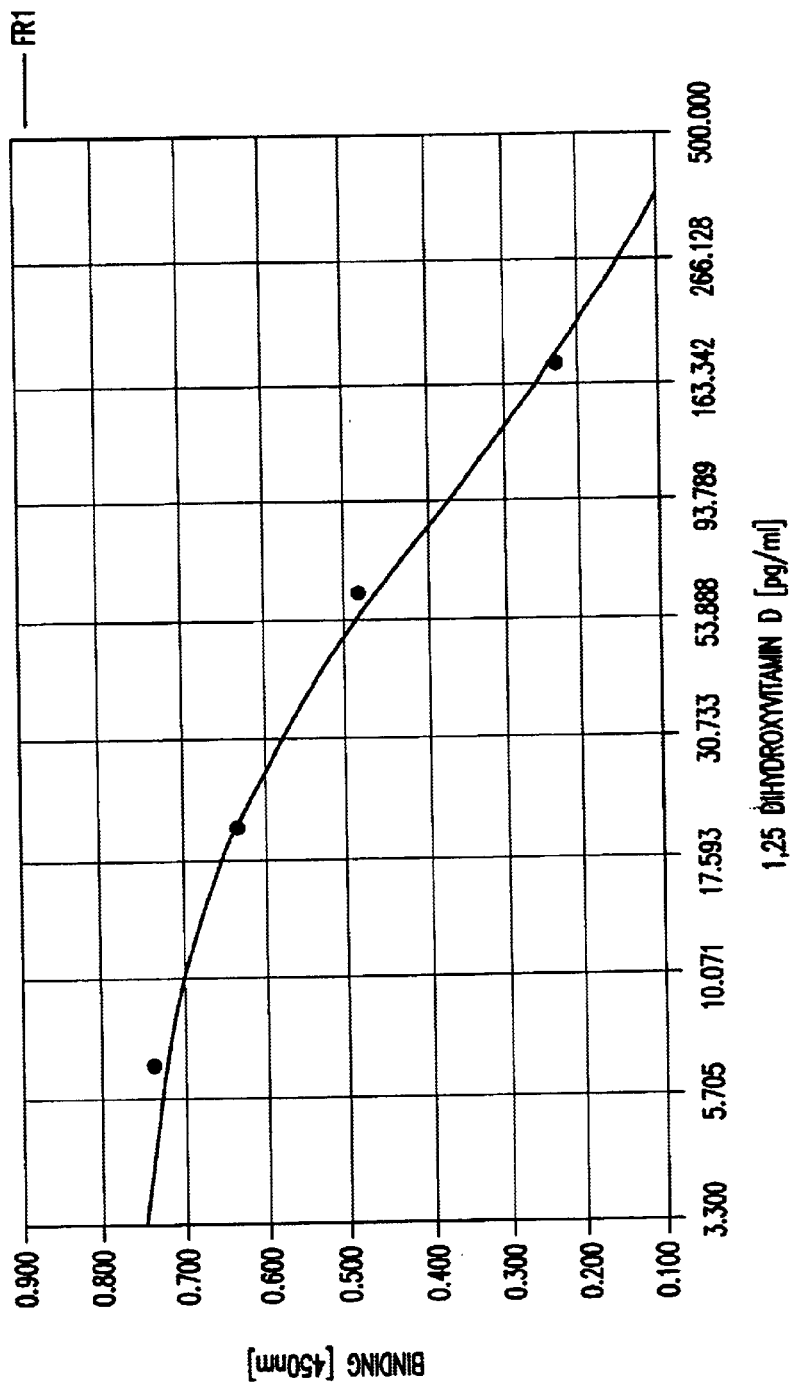
FIG. 5C the calibration curve of a competitive ELISAs for 1,25-dihydroxy vitamin D, analogous to FIG. 2.

FIGS. 5A–C show the typical calibration curves of competitive ELISAs with 25-OH- or 1,25-dihydroxy vitamin-$D_3$-biotin, in accordance with the principle shown in FIG. 2. The quantity of bound vitamin D binding protein was determined by means of a standardised colour reaction with peroxidase-coupled anti-vitamin D binding protein antibodies and tetramethylbenzidine (TMB) as substrate. Alternative substrates would be, for example, OPD (1,2-phenyldiamine×2 HCl), ABTS and others. For the calibration curve, vitamin D samples with concentrations of 0, 8, 20, 50, 125 and 312 nMol/l were employed. The ordinate shows the optical density as the mean value of two measurements at 450 nm; the abscissa shows the concentration of 25-OH- or 1,25-dihydroxy vitamin D in nMol/l.

Figure 6:
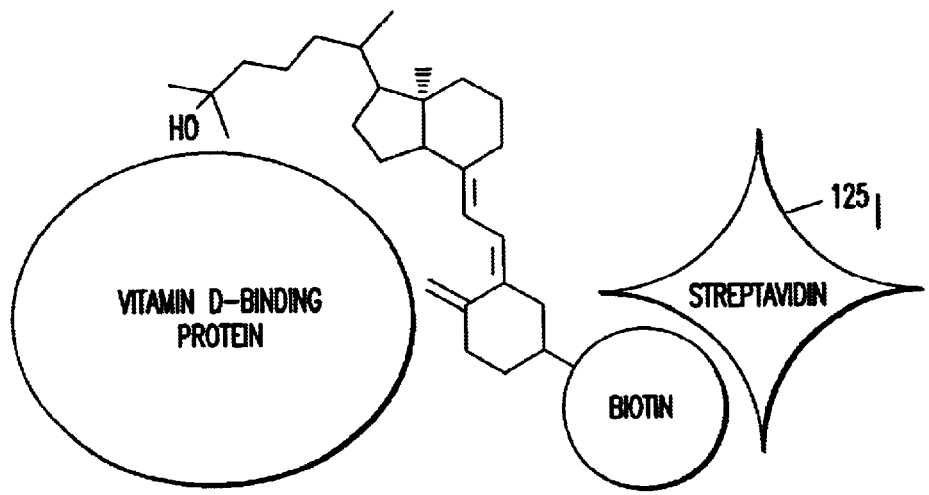
FIGS. 6 and 7 schematic representations of competitive RIAs for 25-OH-vitamin D with the aid of the 25-OH-vitamin D conjugate in accordance with the invention.

FIG. 6 shows the schematic representation of a competitive protein binding test (CPBA), wherein 25-OH-vitamin-$D_3$-biotin and 25-OH-vitamin D, from a standard or sample, compete in liquid phase for the binding site of the vitamin D binding protein. $^{125}$I-labelled streptavidin is employed for the quantitative detection.

Figure 7:
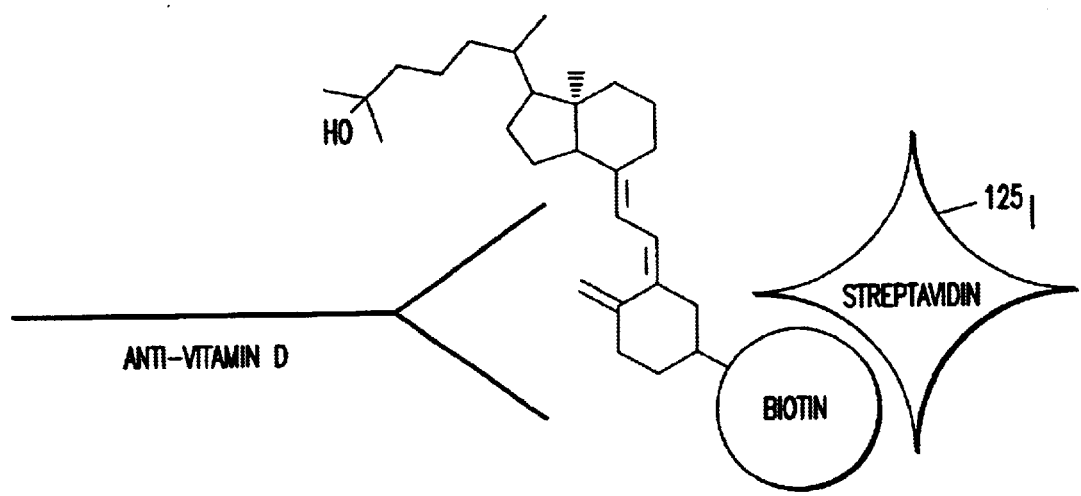

FIG. 7 shows the schematic representation of a competitive radioimmunoassay (RIA), wherein 25-OH-vitamin-D-biotin and 25-OH-vitamin D from a standard or a sample compete in liquid phase for the binding site of an anti-vitamin D-antibody. $^{125}$I-labelled streptavidin is employed for quantitative detection. If the detection is effected by means of a streptavidin which is not radioactive but is labelled with a fluorophore or luminophore, so-called LIA or FIA assays are involved.

Figure 8:
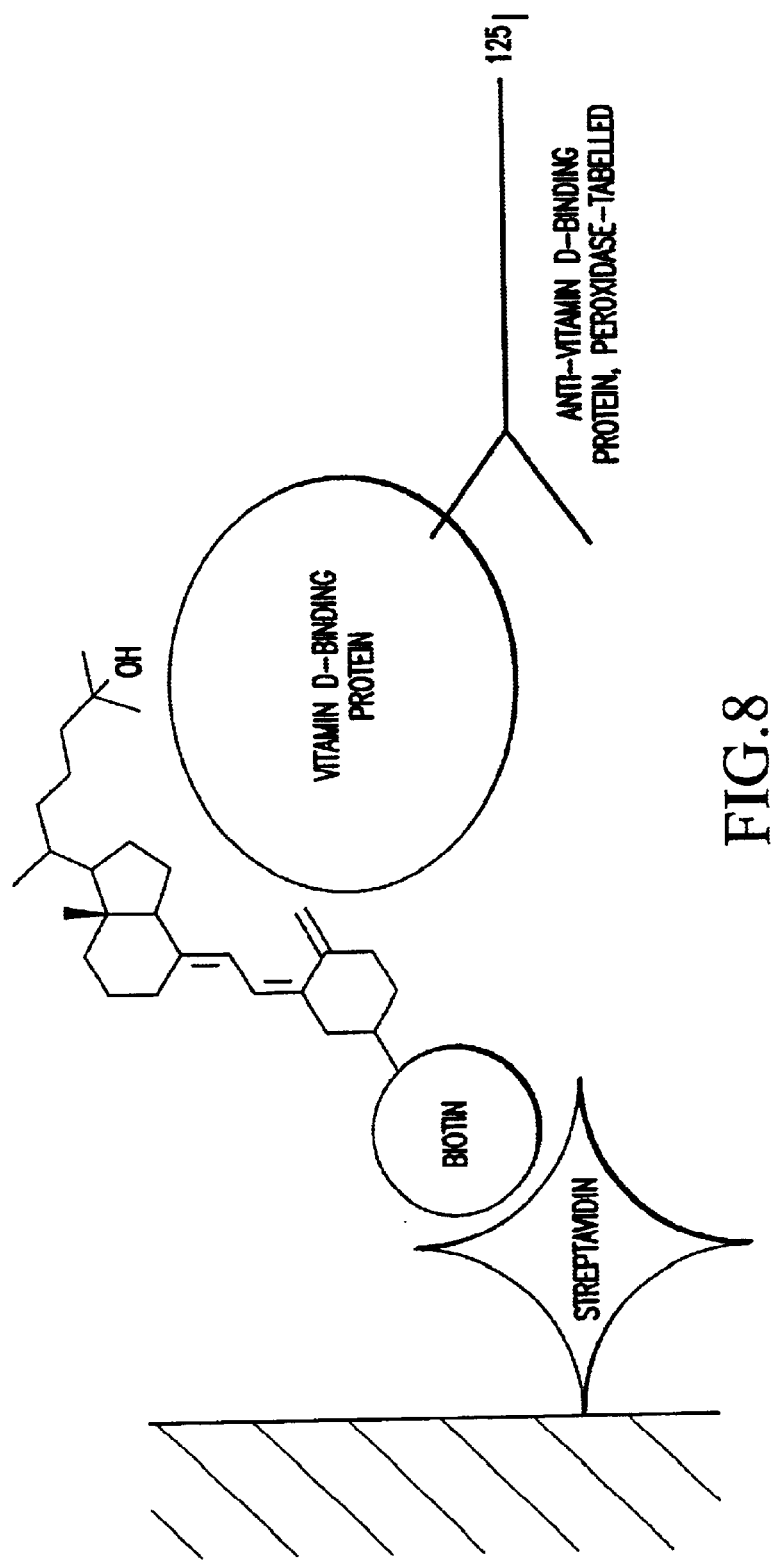
FIGS. 8, 9 and 10 schematic representations of competitive, radioactive IRMAs for 25-OH-vitamin D with the aid of the 25-OH-vitamin D conjugate in accordance with the invention.

FIG. 8 shows schematic representation of a 25-OH-vitamin D-IRMA. First, 25-OH-vitamin-D-biotin is bound to the solid phase via streptavidin. The competitive binding of vitamin D-binding protein to the conjugate and 25-OH-vitamin-$D_3$ from a standard or a sample is then effected in liquid phase. The quantity of the conjugate-bound binding protein is determined with $^{125}$I-labelled antibodies.

Figure 9:
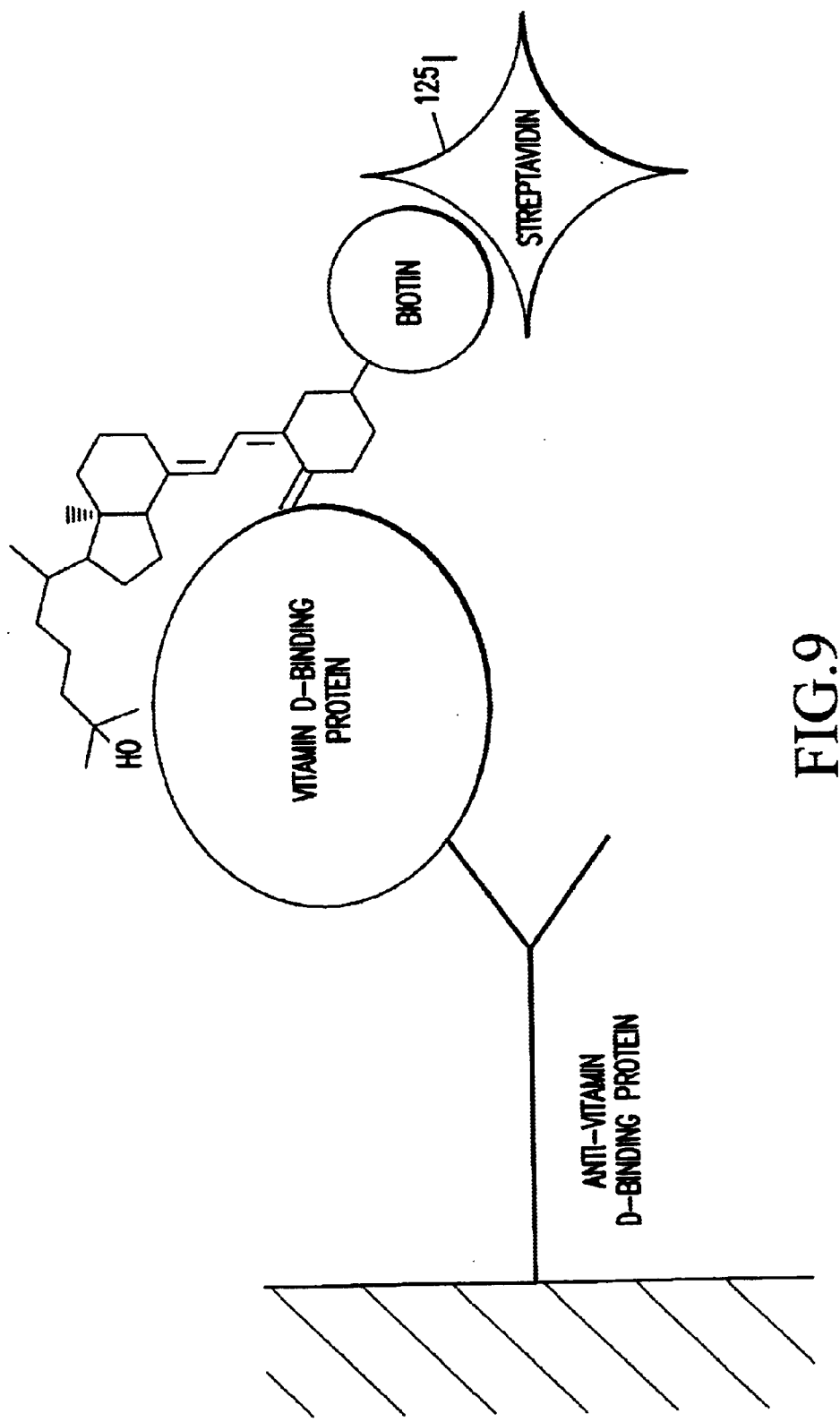

FIG. 9 is the schematic representation of an IRMA sandwich technique (immunoradiometric assay). For this purpose, anti-vitamin $D_3$ antibodies are coupled to the solid phase. Vitamin D binding proteins then bound to these. The competition takes place in the next step between the 25-OH-vitamin D conjugate and 25-OH-vitamin D from a standard or a sample. The determination of the quantity of the bound conjugate is effected by means of a $^{125}$I-labelled streptavidin.

Figure 10:
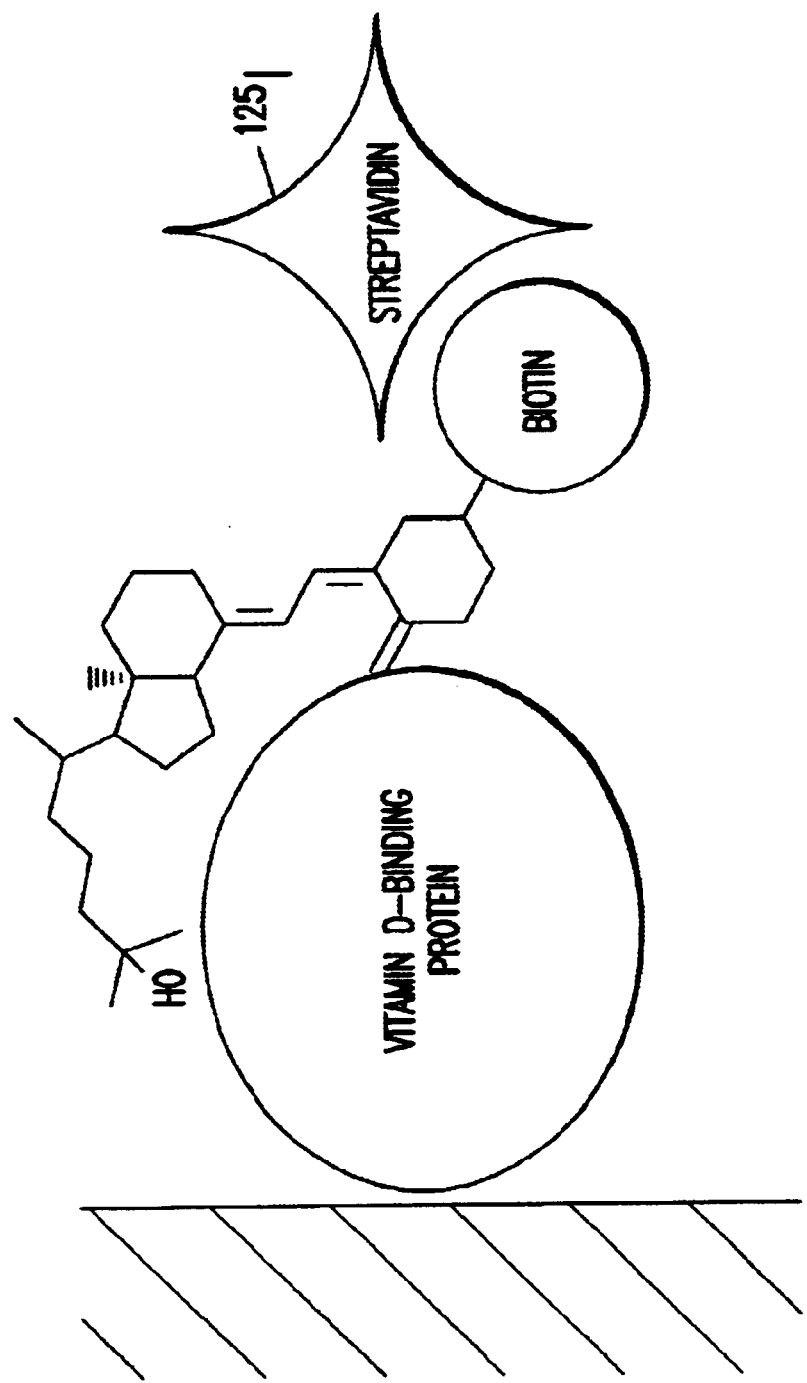

FIG. 10 shows the schematic representation of a further S IRMA sandwich technique. First, vitamin $D_3$ binding proteins are coupled to the solid phase. There is then effected thereupon the competitive binding between the 25-OH-vitamin $D_3$ conjugate and 25-OH-vitamin $D_3$ from a standard or a sample. The quantity of bound conjugate is determined by means of $^{125}$I-labelled streptavidin.

Figure 11:
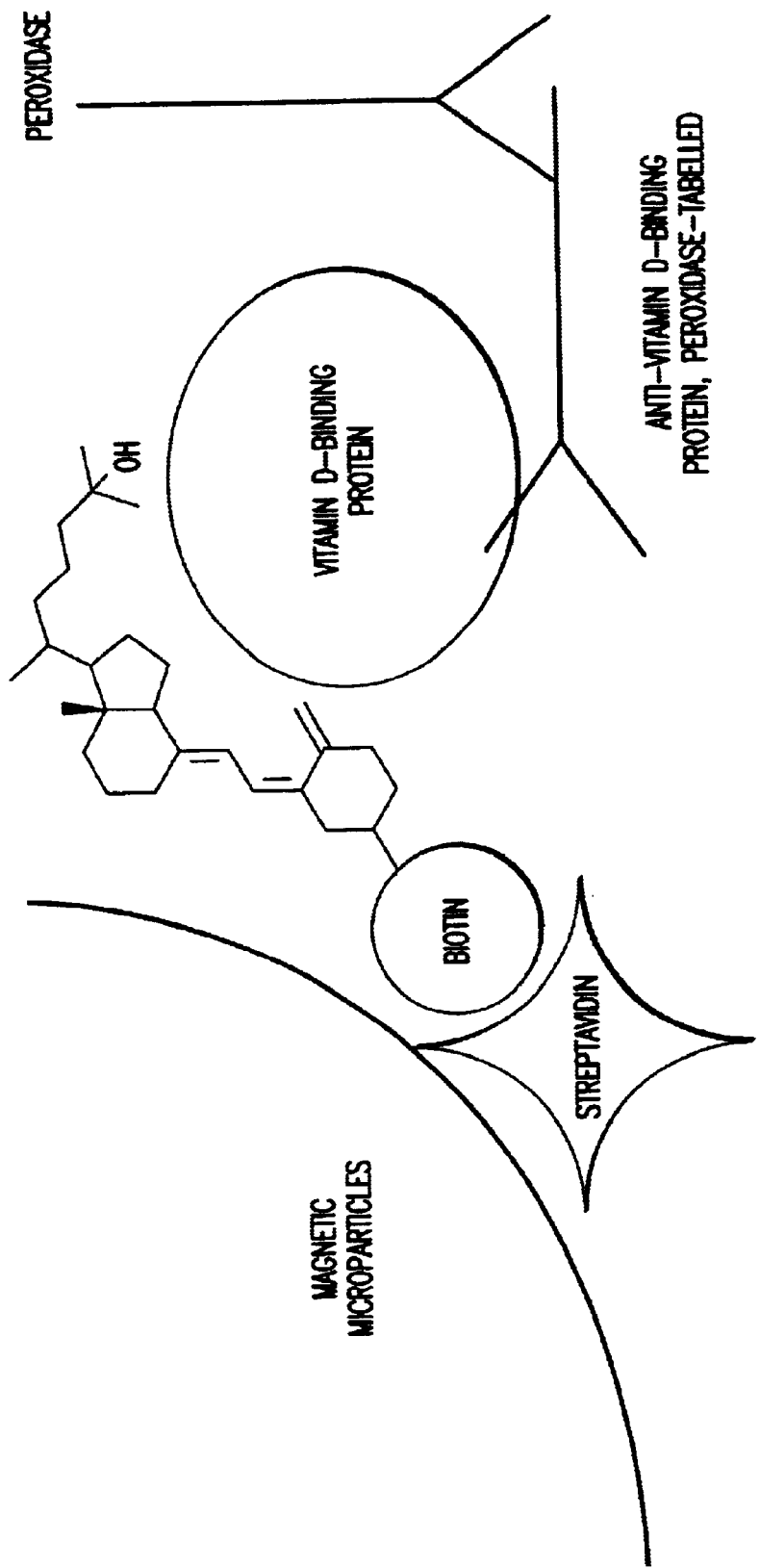
FIGS. 11 and 12 schematic representations of competitive ELISAs with the employment of microparticles.

FIG. 11 shows the schematic representation of a competitive ELISA employing microparticles. Here, 25-OH-vitamin D-biotin is bound to microparticles via streptavidin. 25-OH-vitamin D derivative is then bound thereto. Vitamin D binding protein and the sample concerned are then added in liquid phase. Binding proteins and 25-OH-vitamin $D_3$ from a standard or a sample compete for the binding site of the conjugate. The bound components are separated in that they are held back via the microparticles by a magnet, whereas the remainder with the non-bound substances is removed. The quantity of coupled binding protein is determined in a 2-stage process with a primary antibody against vitamin D binding protein and a secondary peroxidase-labelled antibody.

Figure 12:
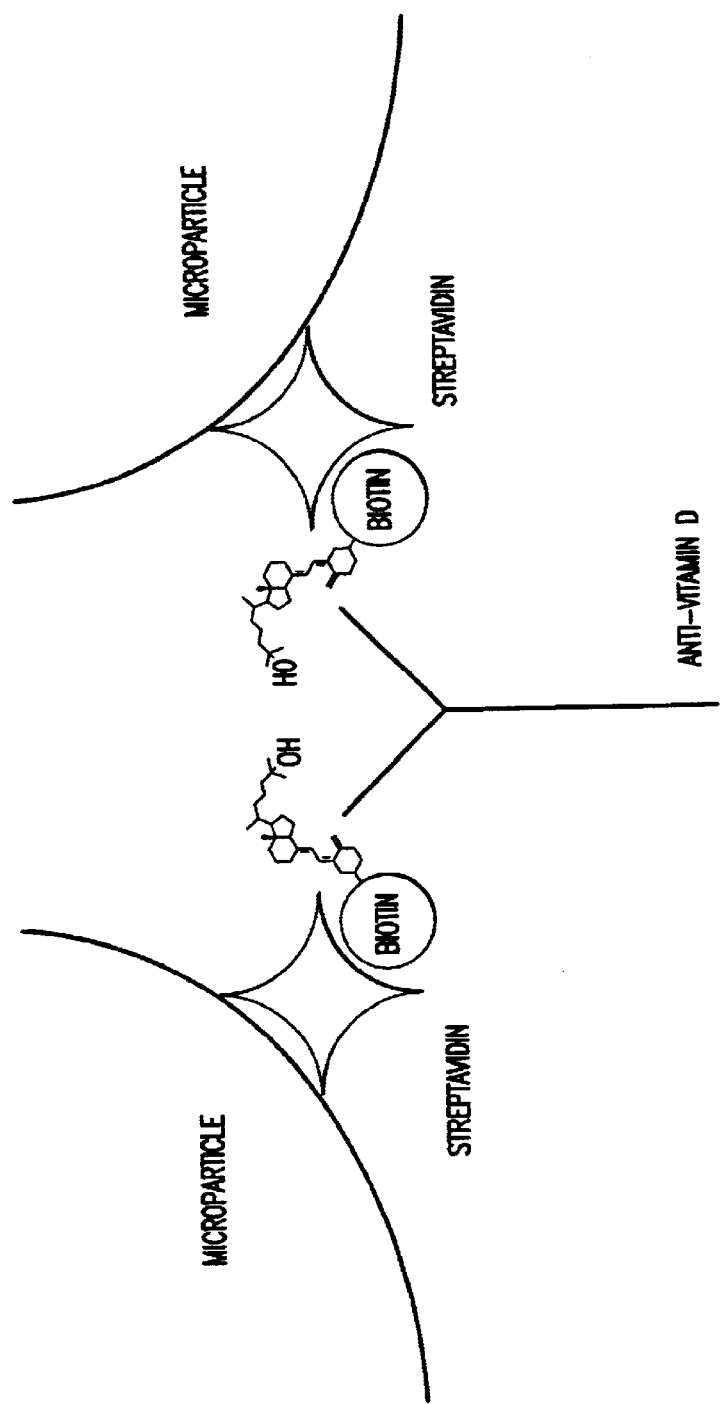

FIG. 12 shows a schematic representation of a competitive ELISA employing microparticles. 25-OH-vitamin-D-biotin is bound to microparticles via streptavidin. Then the liquid sample with 25-OH-vitamin $D_3$ (from a standard or a sample) is added, as is a non-saturating quantity of antibodies. The conjugate and the native vitamin $D_3$ compete for the binding of the antibody. The quantity of bound antibodies is effected by means of agglutination of the microparticles. This can be determined for example directly by means of nephelometric analysis or turbimetric analysis.

Figure 13:
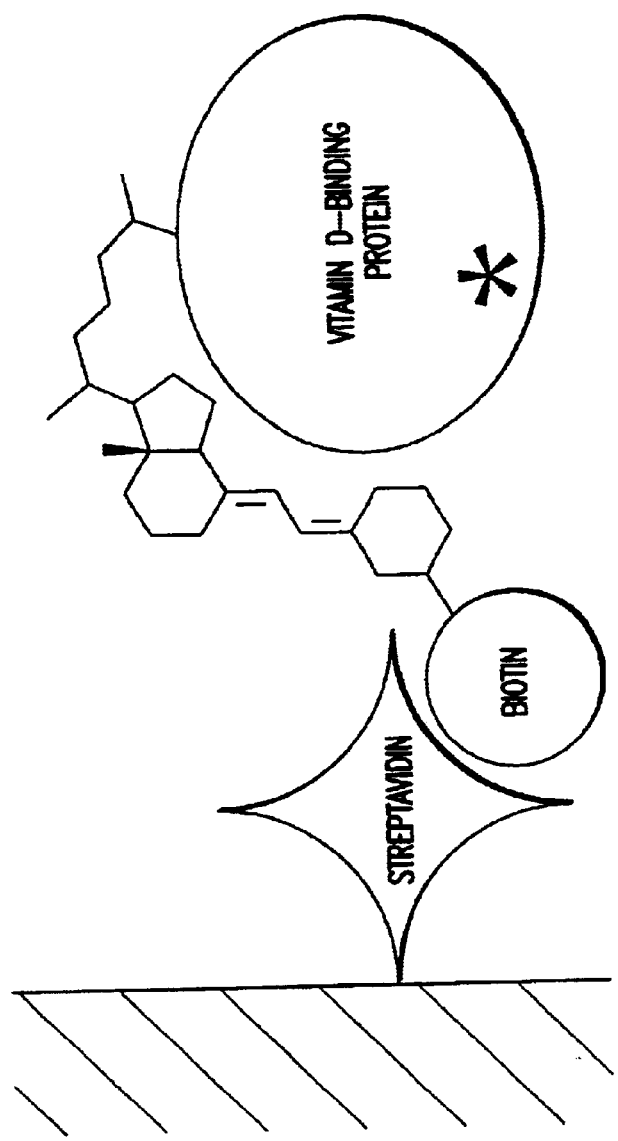
FIG. 13 schematic representations of a competitive binding assay for 25-OH-vitamin D with the aid of a 25-OH-vitamin D conjugate in accordance with the invention and a directly labelled vitamin D binding protein.

FIG. 13 shows the scheme of a competitive binding assay, whereby the vitamin D binding protein is directly labelled, for example radioactively with $^{125}$Iodine, or for an electrochemoluminescence, with ruthenium(II)tris-(bipyridine)-NHS-ester. The marking may also be enzymes such as peroxidase, alkaline phosphatase, β-galactosidase, etc., or may also be FITC.

Figure 14:
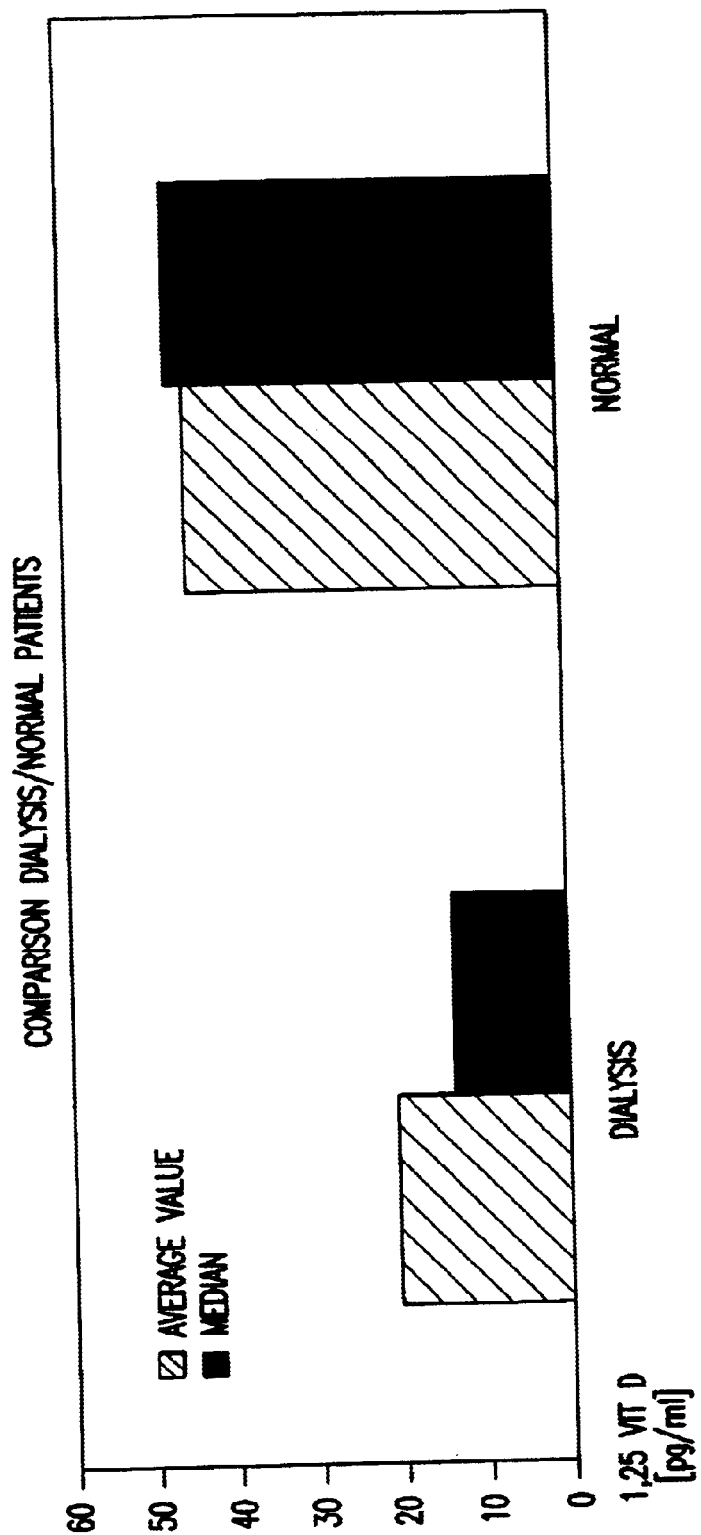
FIG. 14 a block diagram of the comparison of the 1,25-dihydroxy vitamin D-content in serum from dialysis patients and normal patients.

FIG. 14 illustrates in a block diagram the different 1,25-dihydroxy vitamin D contents in serum from dialysis patients and from normal patients.

The known detection methods for proteins such as the competitive ELISA are based on the principle that the compound to be detected competes with a binding protein or conjugate for a binding site. Then, the quantity of bound binding protein or conjugate is determined and on the basis of a calibration curve the concentration of the compound to be detected is determined.

The test principles shown in the Figures can be carried over simply to other vitamin D derivatives. 1α,25-dihydroxy vitamin $D_2$ and $D_3$ are to be particularly mentioned. In this case a binding protein or a receptor or antibody must be selected which specifically recognises the 1α,25-dihydroxy vitamin D analog. The associated bifunctional 1α,25-dihydroxy derivative can be obtained enzymatically by means of reaction of 25-OH-vitamin D-3β-cyanoethylether with 25-OH-vitamin-D-1α-hydroxylase, reduction to the amine and finally the addition of the second functional group. Further, derivatives of vitamin $D_2$ and vitamin $D_3$ are here proposed. The synthesis thereof can be effected through the route set out in Example 1.

EXAMPLES

Example 1

Synthesis of 25-OH-Vit.-$D_3$-3β-3'[6-N-(biotinyl)-hexamido]amidopropylether (4)

All reactions were performed in the dark in a dry nitrogen atmosphere. Intermediate products were stored at −20° C. HPLC-pure solvents were employed. The 25-OH-vitamin $D_3$ was obtained from BIOMOL Feinchemikalien GmbH, Hamburg, the LC-BHNS (Long-Chain-Biotinyl-N-ε-amino caproyl-hydroxy-succinimide ester) from Sigma Chemie, and all further chemicals from Fluka, Darmstadt. The mass spectroscopy (FAB) was carried out with a Finigan-MAT-90, the NMR-measurements with a Bruker-ARX-400 (400 MHz) or a Bruker-ARC-250F (250 MHz).

(i) 25-OH-Vitamin $D_3$-3β-cyanoethylether (2)

5 mg 25-OH-vitamin $D_3$ (12.5 μMol), dissolved in methylene chloride ($CH_2C_2$), was transferred into a vial filled with nitrogen and the solvent was distilled off. The solid remainder was dissolved in 1 ml acetonitrile and mixed with 10 drops of a mixture of tertiary butanol and acetonitrile (9:1 v/v) and 130 μMol acrylonitrile (10 eq.) in 100 μl acetonitrile [stock solution: 86 μl acrylonitrile (1.3 mMol) diluted with acetonitrile to 1 ml]. The clear solution was stirred for 15 minutes at 6° C. 6.25 μMol potassium hydride (0.5 eq.) in 25 μl tertiary butanol/acetonitrile (9:1 v/v) [stock solution: 10 mg KH (250 μMol) in 1 ml tertiary butanol/acetonitrile (9:1 v/v)] was added. The flocculation thereby arising dissolved again immediately. The mixture was stirred at 6° C. Repeated thin layer chromatography (DC) of individual samples with 20% petrolether in methyl-tert.-butylether (MTBE) on silica gel showed that after 10 minutes 90% of the initial compound had been reacted. After 15 minutes a few drops of the reaction mixture were prepared with about 5 drops of water and 0.5 ml MTBE. The thin film chromatography of the organic phase showed no further educt. After 40 minutes the entire reaction mixture was prepared with water/MTBE. 4 mg oleaginous product was obtained.

| IR (NaCl/CH$_2$Cl$_2$): | 3422 | OH |
| --- | --- | --- |
| | 2941, 2872 | CH |
| | 2252 | nitrile |
| | 1105 | ether |

The HPLC-analysis (3% MeOH/CH$_2$Cl$_2$) showed 93% product and 7% educt. Thus, 4 mg product contained 3.7 mg (8.2 μMol) target compound, which corresponds to a yield of 74%.

(ii) 25-OH-vitamin D$_3$-3β-3'amino propylether (3)

3.75 mg (8.3 1Mol) nitrile from (i) was dissolved in 2 ml ether, to which was added 125 μMol lithium hydride dissolved in 1 ml ether (stock solution: 7 mg fresh finely powdered LiH in 7 ml ether) and stirred for 1 hour at room temperature in a nitrogen atmosphere. 169 μMol LiAlH$_4$ was added as suspension in 1 ml ether (base: 18 mg fresh finely powdered LiAlH$_4$ in 3 ml ether). After a further hour the mixture was prepared with 1 ml concentrated KOH, 5 ml H$_2$O and 4×20 ml MTBE. The thin film chromatography of a sample with 1:1 MTBE/petrolether on silica gel showed only the starting point. The diole was at R$_f$ 0.27; the nitrile at R$_f$ 0.4. The substance obtained was processed further without further analysis and purification.

(iii) 25-Hydroxy vitamin D$_3$-3β-3'[6-N-(biotinyl) hexaamido]-amidopropylether (4)

3 mg (6.6 μMol) 25-OH-vitamin D$_3$-3β-amino propylether (3) from (ii) was dissolved in 1 ml dimethylformamide (DMF). Then, in a nitrogen atmosphere, 3 mg (6.6 μMol) LC-BNHS and 1 μl (17.5 μmol) triethylamine were added. Stirring for 18 hours at room temperature took place, the DMF was distilled off and the residue pre-purified with 20% methanol (MeOH) in CH$_2$Cl$_2$. 12 mg (>100%) of the substance so obtained was purified by means of HPLC (conditions: Knauer Kromasil-100, 5 μM, 250×4 mm, 10% MeOH in CH$_2$Cl$_2$, 1.5 ml/min, OD 265 nm, 7 minutes). The yield amounted 1.2 mg (1.5 μMol). This corresponds to 129 referred to the 25-OH-vitamin D$_3$ and 18% referred to the nitrile compound.

TABLE I

Biotin-25-OH-Vitamin D$_3$

| H | Mult | Cc [Hz] | Assignment |
| --- | --- | --- | --- |
| 6.42 | 1 | Dd | 5.7 | NH (Biotin) |
| 6.2 | 1 | D | 11 | 6 |
| 6.0 | 1 | D | 11 | 7 |
| 5.85 | 1 | Dd | 5.7 | NH (Biotin) |
| 5.55 | 2 | M | | 3-O—CH$_2$(28) |
| 5.38 | 1 | S | | NH or OH |
| 5.05 | 1 | D | 2 | 19 |
| 4.83 | 1 | D | 2 | 19 |
| 4.77 | 1 | S | | NH or OH |
| 4.51 | 1 | M | | HC—NH I Biotin |
| 4.33 | 1 | M | | HC—NH II Biotin |
| 3.53 | 1 | M | | 3 |
| 2.53 | 1 | D | 10 | 4 |
| 1.21 | 6 | S | | 26,27-CH$_3$ |
| 0.93 | 3 | D | 6 | 21-CH$_3$ |
| 0.54 | 3 | S | | 18-CH$_3$ |

MS (Finigan MAT 90); (FAB): 797 (MH$^+$) of 5.9.97 and 28.11.97; $^1$H-NMR (Bruker ARX 400) in CDCl$_3$/TMS at 400 MHz. The data of the analysis are shown in table I.

Example 2

Stability of 25-OH-Vit.-D$_3$-3β-3'[6-N-(biotinyl)-hexamido]amidopropylether

In each case 20 mg purified 25-OH-D$_3$-biotin compound (25-OH-vitamin D$_3$-3β-3'[6-N-(biotinyl)-hexamido] amidopropyl-ether) from Example 1 was placed in an NMR test tube to which 1 ml solvent was added. The solvent was a mixture of deuterium chloroform:deuterium acetonitrile: D$_2$O in the ratio 3:2:1 with a pH-value between 4 and 5. The samples were stored for 200 days under the conditions set out below and the NMR spectra were investigated at regular intervals.

Sample 1: light excluded at −20° C.;
Sample 2 light excluded at +4–6° C.;
Sample 3: light excluded at room temperature;
Sample 4: subject to strong light (on a window ledge) at room temperature.

Samples 1 and 2 showed no substantial alteration in NMR-spectrum over the entire time. An HPLC analysis confirmed that samples 1 and 2 were intact even after 200 days in protonic solvent. Sample 3 showed a minimal alteration of NMR spectrum after 100 days. The HPLC analysis indicated that more than 78% of the compound was still intact. Sample 4 was degraded after two months. The investigation of stability shows that the compound is very stable when light is excluded, even in protonic solvent and without cooling.

Example 3

25-Hydroxy Vitamin D-ELISA with 25-Hydroxy Vitamin D$_3$-3β-3'[6-N-(biotinyl)-hexamido] amidopropylether The detection was effected in accordance with the principle illustrated in FIG. 2. For this purpose, 25-OH-vitamin D-3β-3'[6-N-(biotinyl)hexamidol]amidopropylether had to be bound to a solid phase via streptavidin.

(i) Coating a Microtitration Plate with Streptavidin

Into each of the wells of a microtitration plate there was placed 100 ng streptavidin, dissolved in 200 μl 60 nM NaHCO$_3$, pH 9.6, and the plate incubated overnight at 4° C. The streptavidin solution in the well was removed and each well washed five times with 200 μl washing buffer (PBS, pH 7.4 with 0.05% Tween-20). Then, 250 μl assay buffer was placed in each well. For the assay buffer, 5 g casein was dissolved in 100 ml 0.1 N NaOH and topped up with PBS, pH 7.4 to 1 L volume. The solution was boiled for one hour, the volume supplemented to 1 liter with distilled water, the pH value set to 7.4 and 0.1 g thimerosal added to avoid growth of microbes. The wells in the microtitration plate were incubated for 1 hour at room temperature with assay buffer, then the assay buffer was removed and each well washed five times with in each case 200 μl washing buffer.

(ii) Binding of 25-Hydroxy vitamin D$_3$-3β-3'[6-N-(biotinyl)-hexamido]amidopropylether Into each well there was introduced 100 μl biotin-vitamin D-solution (10 ng 25-OH-vitamin D-3β-3'[6-N-(biotinyl) hexamido]amidopropylether in 100 μl washing buffer) and incubated for one hour at room temperature, in the dark whilst being shaken. Then, the biotin-vitamin D-solution was removed from the wells and each well washed five times in each case with 200 μl washing buffer. In the liquid phase, there was effected a competitive binding of vitamin D binding protein in the presence of 25-OH-vitamin D from a standard or a sample.

(iii) Sample Preparation

50 μl serum was mixed by vortexing with 200 μl ethanol$_{abs}$ (pre-cooled to −20° C.) in a 1.5 ml Eppendorf reaction vessel and precipitated for 20 minutes at −20° C. The samples were centrifuged at maximum speed of rotation in an Eppendorf table centrifuge and the result removed and placed in the ELISA.

One can as a rule assume that plasma or serum samples are stable for about two weeks at 4° C. In the case of longer storage they must be deep frozen until they are analysed. Before storage, urine samples must be set to a pH-value between 6 and 8 with 1 N NaOH. Then, they may be stored at 4° C. for about 14 days; in the case of longer storage these also must be deep frozen until the analysis is carried out.

(iv) Competitive Binding

In each case 100 µl vitamin D binding protein, isolated from goat serum (1:15000 in assay buffer with 3% (w/v) PEG 6000) together with 10 µl standard, control or sample (10 µl result from the sample preparation) was placed in the wells. The microtitration plate was incubated for 24 hours at 4° C. in the dark and subject to shaking. Then, the solution was removed from the wells and the wells washed five times in each case with 200 µl washing buffer.

(v) Detection of the Competitive Binding

In each case 100 µl rabbit-anti-vitamin D-binding-protein (1:10000 diluted in assay buffer having 3% (w/v) PEG 6000) was introduced into the wells and incubated for 1 hour in the dark and subject to shaking, at room temperature. The solutions were removed from the wells and each well washed five times with in each case 200 µl washing buffer.

The quantitative determination was effected with 100 µl anti-rabbit-IgG-peroxidase (1:20000 diluted in washing buffer). Incubation took place for 1 hour at room temperature. Thereafter antibody solutions were taken off and each well washed five times in each case with 200 µl washing buffer. For the colour reaction 100 µl tetramethylbenzidine (TMB) substrate solution (ready for use, from NOVUM Diagnostika GmbH, Dietzenbach, Germany) was introduced into the wells. After 30 minutes the colour development was stopped by the addition of 50 µl 2 M $H_2SO_4$ per well. The measurement of the optical density was effected at 450 nm. The following tables II and III show the pipetting scheme for the microtitration plate and the values for the optical density.

As standards there were employed solutions of 25-OH-vitamin $D_3$ in assay buffer with the following concentrations: 0, 8, 20, 50, 125 and 312 nMol/L (see calibration curve in FIG. 5A). As controls or samples there served four serums from patients having a D-hypovitaminosis (sample nos. 24, 203, 963, 965) and four randomly chosen normal serums (sample nos. NP 18, NP 25, NP 34, NP 37—test series 3 and 4). For the vitamin D-deficiency serums additionally the 25-OH-vitamin D concentration was determined by means of competitive binding assay with the aid of $^3$H-25-OH-vitamin D. As a further "controls" there served four solutions for which the respective concentrations of 25-OH-vitamin D were known from other determinations, either from manufacturer information or by means of a competitive binding assay (CBPA) with $^3$H-25-OH-vitamin D.

TABLE II

Sample arrangement

| Pipetting Scheme | Standard nMol/L | Duplicate value of column 1 | Serum sample No. | Duplicate value of column 3 | Controls | Duplicate value of column 5 |
|---|---|---|---|---|---|---|
| Row/Column | 1 | 2 | 3 | 4 | 5 | 6 |
| A | NSB | NSB | 24 | 24 | K1 (CPBA) | K1 (CPBA) |
| B | 0 | 0 | 203 | 203 | K2 (CPBA) | K2 (CPBA) |
| C | 8 | 8 | 963 | 963 | K3 (HPLC) | K3 (HPLC) |
| D | 20 | 20 | 965 | 965 | K4 (HPLC) | K4 (HPLC) |
| E | 50 | 50 | NP 18 | NP 18 | | |
| F | 125 | 125 | NP 25 | NP 25 | | |
| G | 312 | 312 | NP 34 | NP 34 | | |
| H | | | NP 37 | NP 37 | | |

NSB: Non-specific binding buffer (Assay buffer without Vitamin D binding protein)

TABLE III

Measurement values after 30 minutes colour development

| OD 450 nm | Standard | Duplicate value for column 1 | Serum sample No. | Duplicate value for column 3 | Controls | Duplicate value for column 5 |
|---|---|---|---|---|---|---|
| Row/Column | 1 | 2 | 3 | 4 | 5 | 6 |
| A | — | — | 0.947 | 1.023 | 1.903 | 2.300 |
| B | 2.256 | 2.182 | 0.853 | 0.910 | 0.393 | 0.371 |
| C | 1.845 | 1.861 | 0.646 | 0.637 | 1.674 | 1.586 |
| D | 1.432 | 1.456 | 1.429 | 1.303 | 0.578 | 0.634 |
| E | 0.625 | 0.612 | 0.524 | 0.547 | | |
| F | 0.287 | 0.261 | 0.454 | 0.419 | | |
| G | 0.156 | 0.176 | 0.341 | 0.368 | | |
| H | — | — | 0.421 | 0.386 | | |
| $B_{max}$ | 2.801 | 2.676 | | | | |

From the mean values of columns 1 and 2 and the known concentration of 25-OH-vitamin D, the calibration curve shown in FIG. 5A was produced. The ordinate shows the optical density as mean value of the two measurements at 450 nm; the abscissa shows the concentration of 25-OH-vitamin D in nMol/l. The results are summarised in Table V.

Example 4

Comparative Binding Analysis with $^3$H-25-OH-vitamin D as Competitive Partner Insofar as no other indication is given, all reagents, buffers and materials were the same as in above-mentioned Example 3. There served as competitive binding partner (tracer) tritium-labelled 25-OH-vitamin $D_3$. Differing from Example 3, the measurement samples were purified by means of extraction (into individual values). For this purpose, in each case 50 µl sample [non-specific assay buffer NSB, standard, control, patients sample (plasma, serum or urine)] was introduced into a 1.5 ml disposable reaction container, 200 µl acetonitrile added, mixed, the container walls centrifuged free, and the mixture incubated for 20 to 30 minutes at 4° C. The mixture was centrifuged at 1700 ×g for 10 minutes. The determinations were effected with the results using duplicate values.

For this purpose 25 µl clear result was transferred to a glass test tube (or into a special-RIA-container from Sarstedt, Darmstadt) and 10 µl tracer ($^3$H-25-OH-D), 300 µl assay buffer and 100 µl vitamin D-binding protein (not in NSB) added. The test tube contents were mixed, incubated for one hour at 4° C. and, to remove non-bound radioactive tracer, 100 µl activated charcoal suspension (activated charcoal containing phosphate buffer with 0.1% $NaN_3$) was added. The test tube content was mixed, incubated for 3 to 5 minutes at 4° C., and the active charcoal pelletized by means of centrifuging for 10 minutes at 1700 ×g. Then, in each case 400 µl of the result was transferred to a counter container (7 ml) and, after the addition of 2 ml scintillator liquid such as Aquasafe™ 300 or HiSafe™ III, the radio-activity present in the result was counted (2 minutes in a beta-counter). The measurement value for the controls, after production of the calibration curve, are shown in Table V.

The comparison with the ELISA according to Example 3 shows that for both assay procedures (ELISA and CBPA) it is the case that the normal range for 25-OH-vitamin D in plasma or serum is about 25–125 nmol/l. The sensitivity limit of the test systems was determined as $B^0+2SD$. It amounts to about 2.5 nmol/l.

Cross reactions: To serum treated with activated charcoal there was added 25-OH-vitamin $D_2$ (125 nmol/l), 24,25-$(OH)_2$-vitamin $D_3$(250 nmol/1) and 1,25-$(OH)_2$-vitamin $D_3$ (250 nmol/l). The 25-OH-vitamin $D_2$ cross-reacted to 60%, the 24,25-$(OH)_2$-vitamin $D_3$ cross-reacted to 100%, whereas the 1,25-$(OH)_2$-vitamin $D_3$ show no cross-reactivity. Similar results have been found or expected also for multifunctional 25-OH-vitamin D conjugate in accordance with the invention.

Reproducibility: In repeat measurements (n=11) of a sample containing 25-dihydroxy vitamin $D_3$ the following results were achieved. Similar applies also for measurements with the aid of the multifunctional 25-OH-vitamin D conjugate in accordance with the invention:

TABLE IV

| | Intra-assay variance: | | |
|---|---|---|---|
| | Number | Mean value nmol/l | Variance % |
| Sample 1 | 32 | 11.3 | 12.5 |
| Sample 2 | 32 | 318 | 7.2 |

| | Inter-assay variance: | | |
|---|---|---|---|
| | Number | Mean value nmol/l | Variance % |
| Sample 1 | 9 | 9.9 | 17 |
| Sample 2 | 9 | 310 | 11 |

| | Clinical: | |
|---|---|---|
| | Number | Mean value nmol/l |
| Normal persons | 35 | 54 |
| Patients having hip joint fractures | 43 | 9.5 |

For the samples mentioned in Example 3 the following 25-OH-vitamin D concentrations were determined with the methods according to Examples 3 and 4.

TABLE V

| Serum sample No. | ELISA with 25-OH-D-Biotin nMol/L | CBPA with $^3$H-25-OH-D nMol/L | Controls | ELISA with 25-OH-D-Biotin nMol/L | Alternative determination nMol/L |
|---|---|---|---|---|---|
| 24 | 32.9 | 33.3 | K1 | Not measured | 20 (a) |
| 203 | 36.8 | 29.19 | K2 | 76.8 | 75–125 (a) |
| 963 | 48.9 | 38.4 | K3 | 15.0 | 20–33 (b) |
| 965 | 21.8 | 15.8 | K4 | 51.3 | 72–120 (b) |
| NP 18 | 57.0 | | | | |
| NP 25 | 67.9 | | | | |
| NP 34 | 82.4 | | | | |
| NP 37 | 72.9 | | | | |

(a) CBPA with $^3$H-25-OH-D
(b) Manufacturer information

The values indicated by the manufacturers were in general higher that the concentrations determined in the competitive binding assay. This suggests that in the supplied samples a significant part of the 25-OH-vitamin D had already decayed or transformed through the action of light.

Example 5

Checking of the ELISA-determination by Means of HLPC

Thus, for various samples the 25-OH-vitamin D concentration was determined by means of the ELISA according to Example 3 and, for the purpose of checking, by means of HPLC. For the calibration curve, standards were employed having vitamin D, concentrations of 0, 8, 20, 50, 125 and 312 nMol/l. All samples and standards were measured with duplicate values. The 25-OH-vitamin $D_3$-concentration of the samples was then determined on the basis of the calibration curve from the mean of the duplicate values.

The results are shown in the following table VI.

TABLE VI

| | 25-OH-Vitamin $D_3$ (nMol/L) | |
|---|---|---|
| Sample | HPLC | ELISA |
| 1 | 20–33 | 30 |
| 2 | 72–120 | 76 |

TABLE VI-continued

| | 25-OH-Vitamin $D_3$ (nMol/L) | |
| Sample | HPLC | ELISA |
| --- | --- | --- |
| 3 | 79–102 | 96 |
| 4 | <15 | <Sensitivity limit |
| 5 | <15 | 7.4 |

Example 6

Long Term Stability of 25-hydroxy Vitamin D-conjugate in the ELISA Detection

Calibration curves were repeated with the same standard solutions and reagents according to Example 3, after 60 and 100 days, in order to determine to what extent an ELISA detection using the biotin-25-OH-vitamin D-conjugate in accordance with the invention changed with the passage of time, when the reagents were stored in the interim at 4 to 6° C. in the dark. The table below shows the respective optical densities after 30 minutes development (see Example 3).

TABLE VII

| Standard nMol/L | Standard | Duplicate value for column 1 | After 60 Days | Duplicate value for column 3 | After 100 Days | Duplicate value for Column 5 |
| --- | --- | --- | --- | --- | --- | --- |
| | 1 | 2 | 3 | 4 | 5 | 6 |
| NSB | — | — | 0.191 | 0.280 | 0.088 | 0.109 |
| 0 | 2.256 | 2.182 | 2.227 | 2.285 | 1.471 | 1.562 |
| 8 | 1.845 | 1.861 | 2.041 | 2.125 | 1.345 | 1.366 |
| 20 | 1.432 | 1.456 | 1.860 | 1.903 | 1.079 | 1.060 |
| 50 | 0.625 | 0.612 | 1.293 | 1.214 | 0.610 | 0.690 |
| 125 | 0.287 | 0.261 | 0.606 | 0.615 | 0.442 | 0.329 |
| 312 | 0.156 | 0.176 | 0.448 | 0.434 | 0.293 | 0.257 |

If the values of the various calibration curves, deducting the respective non-specific binding, are presented in a diagram (see FIG. 5B) it can readily be seen that the calibration curves have the same shape apart from a relative vertical displacement. This shows that the sensitivity and specificity of the ELISA test had not changed over the above-mentioned period of time.

Example 7

25(OH)-vitamin $D_3$-ELISA-MTP with Anti-vitamin-D-binding Protein

The trial was effected in substance in accordance with the protocol of Example 3 and with the principle illustrated in FIG. 4. The following buffers were employed: a) washing buffer: PBS, pH 7.4 with 0.05% Tween-20; b) assay buffer: 5 g casein was dissolved in 100 ml 0.1 N NaOH and supplemented with PBS, pH 7.4 to 1 1. Then 3% (w/v) PEG-6000 and 0.1 g Thimerosal™ were added. All incubations were effected in the dark and subject to shaking.

(i) Coating the Microtitration Plate

Into the wells of a microtitration plate there were introduced in each case 100 μl rabbit-anti-vitamin D-binding protein in 60 mM $NaHCO_3$, pH 9.6, and the plate incubated overnight at 4° C. The solutions were removed and each well washed five times with 200 μl washing buffer. Then, 250 μl assay buffer was introduced into each well and the plate incubated for 1 hour at room temperature. The assay buffer was removed and each well was washed five times with in each case 200 μl washing buffer.

(ii) Sample Preparation

50 μl serum, plasma or standard was mixed in a 1.5 ml Eppendorf reaction container with 200 μl ethanol$^{abs}$ (pre-cooled to −20° C.), vortexed and then precipitated for 20 minutes at −20° C. The samples were centrifuged in an Eppendorf table centrifuge at maximum rotations. The result was taken and employed in the ELISA.

(iii) ELISA

Firstly, into each individual well 100 μl vitamin D-binding protein, diluted in assay buffer, was introduced and incubated for 1 hour at room temperature. The plate was then knocked out and each individual well washed five times in each case with 200 μl washing buffer.

Thereafter, there was introduced into the wells in each case 100 μl biotin-vitamin D, diluted in assay buffer, together with 10 μl standard, sample or control. The plate was incubated for 24 hours at 4° C. The solutions were again removed and each well washed five times in each case with 200 μl washing buffer.

As a third step there was introduced into the wells in each case 100 μl peroxidase-coupled streptavidin in a 1:10000-dilution in washing buffer, and incubated for 45 minutes at room temperature. The plate was knocked out and each well washed five times in each case with 200 μl washing buffer.

For the colour reaction, there was introduced into each well 100 μl TMB-substrate solution. After sufficient colour development (30 minutes) the reaction was stopped with 50 μl 2M $H_2SO_4$ per well. The measurement of the optical density was defected at 450 nm. Similar to same results were obtained as in Example 3 or table V.

Example 8

Content of a Test Pack or a Reagent Set for the Detection of 25-hydroxy Vitamin D and 1α,25-dihydroxy Vitamin D Content of the test pack or test reagents and their preparation:

Standards, for example 6 vials of 25-OH-vitamin D standards with the concentrations 0, 8, 20, 50, 125 and 312 nmol/l; ready for use in washing buffer.

Microtitration plates, for example coated with streptavidin, sterile packed and pre-washed.

Buffer solutions, for example washing buffer, NSB-buffer and assay buffer, stopper solution.

Controls, for example 2 vials 25-OH-vitamin D controls in human serum. Control 1 (30 nmol 25-OH-D/L), control 2 (80 nMol 25-OH-D/L).

Tracer, for example a vial with biotin-vitamin D (25-OH-vitamin $D_3$-3β-3'[6-N-(biotinyl) -hexamidol] amidopropylether) in washing buffer (100 ng/ml).

Vitamin D-binding protein, for example a vial with binding protein from goat serum in phosphate buffer with 0.1% $NaN_3$ as stabilising agent.

Marker, for example a vial of anti-rabbit-IgG-peroxidase in washing buffer.

TMB-developer-solution, for example a vial of stabilised tetramethylbenzidine-developer solution in washing buffer.

Example 9

ELISA for the Quantitative Detection of 1,25-dihydroxy Vitamin D

The detection of 1,25-vitamin $D_3$ was effected in accordance with the principle illustrated in FIG. 2, except that 1,25-dihydroxy vitamin $D_3$-biotin compound served as tracer. In the competition, 1,25-dihydroxy vitamin $D_3$ from a standard or a sample, together with a 1,25-dihydroxy vitamin D binding protein, a monoclonal mouse-anti-1α,25-dihydroxy vitamin D-antibody (B. Mawer et al. in Steriods, 1985, 46, 741–754), were brought together. The 1,25-dihydroxy vitamin $D_3$ from a standard or a sample and the immobilised 1,25-dihydroxy vitamin $D_3$-biotin compound then compete for the binding site of the antibody. The detection is effected by means of peroxidase-labelled antibodies (goat-anti-mouse-IgG-POX).

Figure 1:
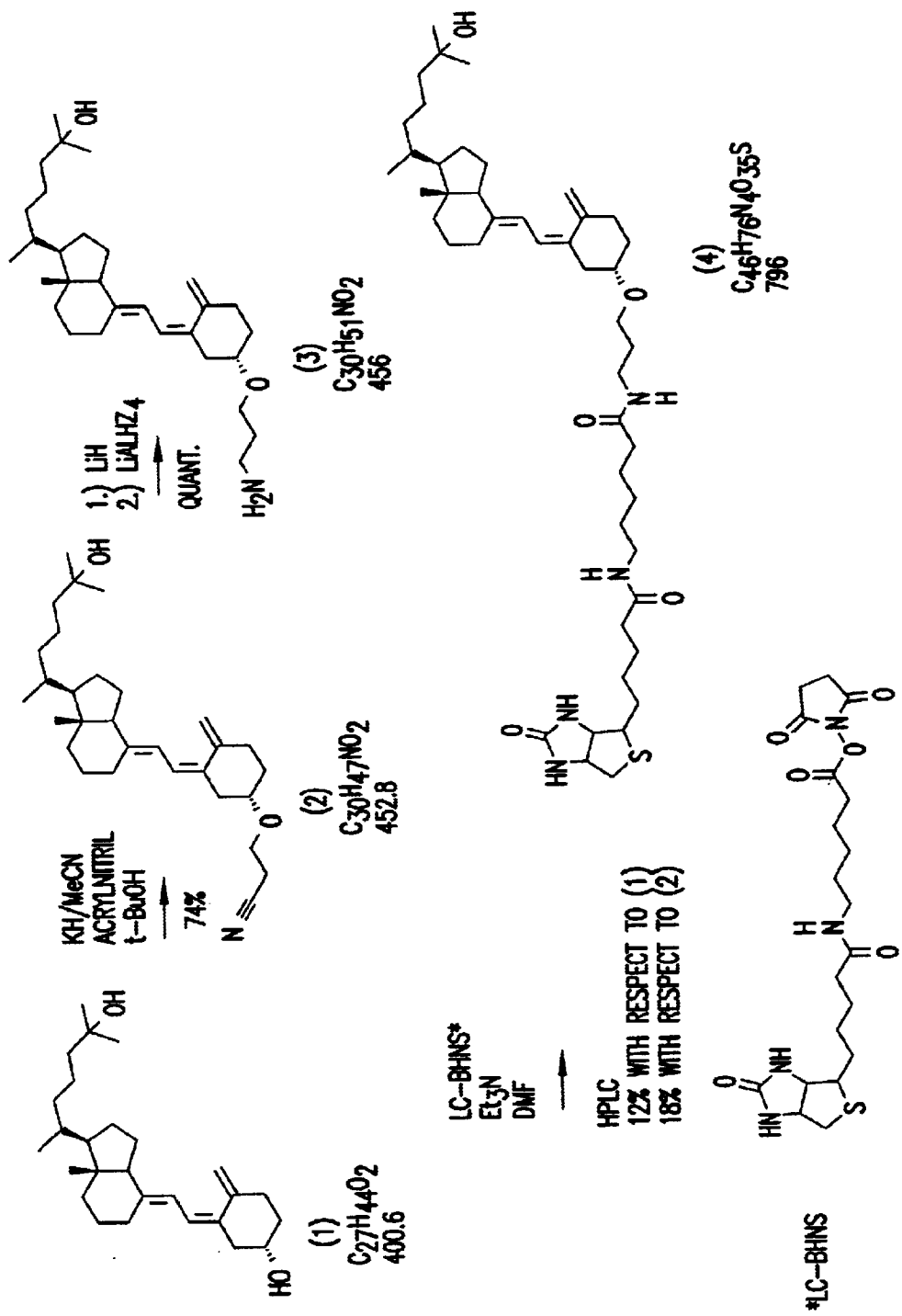
FIG. 1 the schematic path of synthesis for the bifunctional vitamin D derivative 25-hydroxy vitamin-$D_3$-3β-3'[6-N-(biotinyl)hexamido]amidopropylether) in accordance with the invention.

(i) The coating of the microtitration plate with streptavidin was effected as in Example 3, whereby however the washing buffer contained 0.1% Triton™ X-100 as a detergent. Otherwise than as in example 3, the wells in the microtitration plate were no longer washed with washing buffer after the treatment with streptavidin solution, but in each case treated for 1 hour with 250 μl aqueous sorbitol solution (Karion™ F 1:4 in water). The binding of the tracer (1,25-dihydroxy vitamin D-biotin) was effected as in Example 3, except that there was introduced into each well 200 μl tracer solution (20 ng 1,25-dihydroxy vitamin $D_3$-3β-3'[6-N-(biotinyl)-hexamido]-amidopropylether in washing buffer). The 1,25-dihydroxy vitamin D-biotin was synthesised as schematically illustrated in FIG. 1, except that after the first step the excess 3-cyanoethylated 1-OH-vitamin D intermediate compound was isolated. There can however, also be isolated as desired one of the following intermediate compounds or, after a mixed synthesis, specifically the 1,25-dihydroxy vitamin $D_3$-3β-3'[6-N-(biotinyl)-hexamido] amidopropylether by means of HPLC.

(ii) Since in human serum the ratio of 25-OH-vitamin $D_3$ to 1,25-dihydroxy vitamin $D_3$ as rule is in the range of 1000:1 the quantitative detection of 1,25-dihydroxy vitamin D requires a thorough preparation of the samples by means of a combined distribution and absorption chromatography. In the first step, for this purpose, Extrelut™ Kieselguhr columns (Merck, Darmstadt) are brought to equilibrium each with 500 μl tris-buffer and then there is applied to the columns in each case 500 μl of a standard, control or investigation sample—in duplicates; the samples can then draw into the columns for 10 minutes. The separation of the vitamin D-compounds from the Extrelut™ columns was effected by means of four times 1 ml diisopropylether at intervals in each case of 3minutes. The Extrelut™ extract was directly transferred to a silica cartridge (Merck, Darmstadt) and the Extrelut™ columns disposed of. The silica columns were washed five times with 2 ml isopropanol/hexane (4/96 v/v) and 3 times with 2 ml isopropanol/hexane (6/94 (v/v)). The 1,25-dihydroxy vitamin D was then eluded from the silica columns with two times 2 ml isopropanol/hexane (25/75 v/v) and dried in a nitrogen atmosphere at 37° C. or in a vacuum centrifuge. The standard and investigation samples were finally taken up in 20 μl ethanol p.a., in each case with 200 μl mouse-anti-1,25-dihydroxy vitamin D-antibody solution (1:150000 in RRA assay buffer: 50 mM $KH_2PO_4$, 15 mM KCl, 1.25 mM EDTA, 3 mM mercaptoethanol, pH 7.5) and pre-incubated for 1 hour at room temperature—as far as possible at the same time as the application of the 1,25-dihydroxy vitamin D-biotin tracer to the streptavidin treated microtitration plate.

(iii) The wells of the tracer-coated microtitration plate were washed five times in each case with 300 μl Triton™ washing buffer and knocked out onto absorptive paper. Then, 200 μl antibody sample solution from the pre-incubation was transferred into the wells and incubated for 1 hour in the dark and subject to shaking at room temperature. After the removal of the solutions from the wells they were washed five times in each case with 200 μl washing buffer. The quantitative determination was effected analogously to Example 3 by means of 1 hour incubation with 200 μl rabbit-anti-mouse-IgG-peroxidase (1:10000 in washing buffer), at room temperature, five times washing of the wells with 300 μl washing buffer, a colour reaction in the dark with 200 μl TMB substrate solution (ready for use from NOVUM Diagnostika GmbH, Dietzenbach) stopping of the colour reaction after 15 minutes by means of the addition of 50 μl 2 M $H_2SO_4$ and determination of the extinction at 450 nm.

The following table VIII shows the results of the 1,25-dihydroxy vitamin D determination in serum from 11 dialysis patients and six randomly chosen normal persons. For determination of the calibration curve or as standard, there were employed solutions of 1,25-dihydroxy vitamin D in assay buffer with the following concentration: 0, 6.6, 20, 60 and 180 pg/ml (see calibration curve in FIG. 5C).

TABLE VIII

| Pipetting scheme | Standard 1,25-OH-Vit. D (pg/ml) | Remarks | | OD 450 nm | Double value | Mean value | Standard deviation |
|---|---|---|---|---|---|---|---|
| 1 | 0 | Calibration | | 0.784 | 0.781 | 0.782 | 0.002 |
| 2 | 6.6 | curve - | | 0.732 | 0.741 | 0.737 | 0.006 |
| 3 | 20 | See FIG. 5c | | 0.682 | | 0.628 | |
| 4 | 60 | Desired range: | 23–63 pg/ml | 0.484 | | 0.484 | |
| 5 | 180 | Mean: | 43.21 pg/ml | 0.233 | | 0.233 | |
| Control Serum 98-08-295 | 50.1 | S.D.: | 6.62 pg/ml | 0.493 | | | |

| Sample Number | Measured value (pg/ml) | | | | | | |
|---|---|---|---|---|---|---|---|
| 1 | 6.5 | Serum samples | | 0.705 | 0.733 | 0.719 | 0.020 |
| 2 | 39.1 | from dialysis patients | | 0.564 | 0.508 | 0.536 | 0.040 |
| 3 | 57.8 | Mean value: | 20.5 | 0.475 | 0.458 | 0.466 | 0.012 |
| 4 | 12.2 | S.D. | 17.2 | 0.672 | 0.687 | 0.679 | 0.010 |
| 5 | 0.3 | Median | 13.4 | 0.776 | 0.774 | 0.775 | 0.002 |
| 6 | 4.0 | | | 0.667 | 0.816 | 0.741 | 0.105 |
| 7 | 13.4 | | | 0.642 | 0.700 | 0.671 | 0.041 |

TABLE VIII-continued

| | | | | | | | |
|---|---|---|---|---|---|---|---|
| 8 | 39.4 | | | 0.565 | 0.504 | 0.535 | 0.043 |
| 9 | 22.1 | | | 0.619 | 0.618 | 0.000 | |
| 10 | 22.6 | | | 0.531 | 0.700 | 0.616 | 0.119 |
| 11 | 8.6 | | | 0.705 | | 0.705 | |
| Comp. samples | | | | | | | |
| 1 | 52.9 | Serum sample from | | 0.502 | 0.464 | 0.483 | 0.027 |
| 2 | 42.6 | normal persons | | 0.518 | 0.525 | 0.522 | 0.005 |
| 3 | 35.3 | Mean value | 46.0 | 0.522 | 0.583 | 0.553 | 0.043 |
| 4 | 32.9 | S.D | 9.7 | 0.571 | 0.556 | 0.563 | 0.010 |
| 5 | 59.2 | Median | 47.8 | 0.410 | 0.514 | 0.462 | 0.073 |
| 6 | 53.1 | | | 0.485 | 0.480 | 0.482 | 0.003 |

FIG. 14 illustrates in a bar chart once again the values found for dialysis and normal patients, in accordance with which values the serum of dialysis patients on average contains significantly less active 1,25-dihydroxy vitamin D. The great variance of the values for the dialysis patients shows also the need to more closely monitor the content of active 1,25-dihydroxy vitamin D in the serum of dialysis patients, in order better to counter the typical consequences of a vitamin D deficiency.

What is claimed is:

1. A method of obtaining a vitamin D compound of the formula:

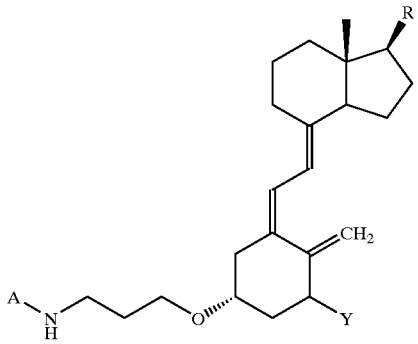

wherein:
R represents a 25-hydroxy side-group of vitamin $D_2$ or of vitamin $D_3$;
Y represents hydrogen or hydroxy;
A represents a functional group, coupled via a spacer group, which can be bound by a protein with high affinity; comprising;
a) cyanoethylating the 3-hydroxy group of a vitamin D starting compound in the presence of potassium hydride and tertiary butanol;
b) adding lithium hydride and converting the 25-hydroxy group into the lithium alcoholate and subsequently reducing the nitrile group with lithium aluminum hydride; and
c) linking a spacer group together with a functional group A on the amino propylether side chain.

2. The method according to claim 1, wherein the functional group A is selected from biotin, digoxigenin, amino acids, characteristic amino acids and peptide sequences, FITC, proteins and peptide groups, protein-A, protein G and vitamin D derivatives.

3. The method according to claim 1, wherein the functional group A is 25-hydroxy vitamin D or 1α,25-dihydroxy vitamin D.

4. The method according to claim 1, wherein the functional vitamin D group is coupled in the 3β-position via an ether bridge with the spacer group.

5. The method according to claim 1, wherein step c) is effected with biotinyl-n-ε-amino caproyl-hydroxy-succinimide ester (LC-BHNS) or an activated biotinylation reagent.

6. Method according to claim 1, wherein the spacer group is an amino carboxylic acid radical, an amino undecanoic acid radical or an amino polyether radical.

7. A method of producing a 3-amino propylether-25-hydroxy or 3-amino propylether-1α,25-dihydroxy vitamin D intermediate compound, comprising;
a) cyanoethylating the 3-hydroxy group of a vitamin D starting compound in the presence of potassium hydride and tertiary butanol;
b) adding lithium hydride and converting the 25-hydroxy group into the lithium alcoholate and subsequently reducing the nitrile group with lithium aluminum hydride.

8. A vitamin D compound of the formula:

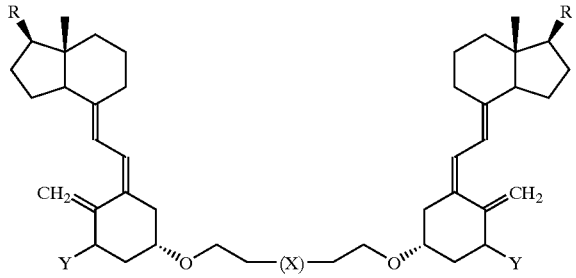

wherein;
R represents a 25-OH side group of vitamin D, or
Y represents hydrogen or hydroxyl and
X represents a substituted or non-substituted hydrocarbon group of 0.8 to 4.2 nm length, which optionally contains the heteroatoms S, O, N, and P.

9. The vitamin D compound according to claim 8, obtained by a process comprising
a) cyanoethylating the 3-hydroxy group of a vitamin D starting compound in the presence of potassium hydride and tertiary butanol;
b) adding lithium hydride and converting the 25-hydroxy group into the lithium alcoholate and subsequently reducing the nitrile group with lithium aluminum hydride to generate an amine; and
c) linking two amino-vitamin D groups together by condensing with a dicarboxylic acid.

* * * * *